United States Patent [19]
Milbrandt et al.

[11] Patent Number: 6,140,117
[45] Date of Patent: Oct. 31, 2000

[54] NINJURIN

[75] Inventors: Jeffrey Milbrandt, St. Louis, Mo.; Toshiyuki Araki, Kyoto, Japan

[73] Assignee: Washington University, St. Louis, Mo.

[21] Appl. No.: 08/672,850

[22] Filed: Jul. 24, 1996

[51] Int. Cl.[7] .............................. C12N 15/12; C12N 5/02
[52] U.S. Cl. ........................... 435/325; 536/23.5; 435/6; 435/69.1; 435/320.1; 435/252.3
[58] Field of Search ................................ 536/23.5; 435/6, 435/69.1, 320.1, 325, 252.3

[56] References Cited

FOREIGN PATENT DOCUMENTS

| | | |
|---|---|---|
| 0 572 664 | 12/1993 | European Pat. Off. . |
| 0 679 716 | 11/1995 | European Pat. Off. . |
| 96/04396 | 2/1996 | WIPO . |

OTHER PUBLICATIONS

Dickson, G. et al., *Cell*, 50:1119–30, 1987.

Hasegawa et al., "Localization of E–Cadherin in Peripheral Glia After Nerve Injury and Repair," *Medline (U.S. National Library of Medicine (NLM))*, Accession No. 96228259 from *Journal of Neuropathology and Experimental Neurology*, 55(3):Abstract only (1996).

Lee et al., "Comparative Expressed–Sequence–Tag Analysis of Differential Gene Expression Profiles in PC–12 Cells Before and After Nerve Growth Factor Treatment," *EMBL/Genbank Databases*, Accession No H33513, Sequence Reference RS5132 (1995).

Okubo et al., "Gene Expression of Human Promyelocytic Cell Line HL60 Before and After Induction of Differentiation. A New Application of 3' Directed cDNA Sequencing," *EMBL/Genbank Databases*, Accession No. D20064, Sequence Reference HSGS01036 (1994).

Hillier et al., "The WashU–Merck EST Project," *EMBL/Genbank Databases*, Accession No. H91351, Sequence Reference HS351243 (1995).

Hillier et al., "The WashU–Merck EST Project," *EMBL/Genbank Databases*, Accession No. W38567, Sequence Reference HS567344 (1996).

Araki et al., "Ninjurin, A Novel Adhesion Molecule, Is Induced by Nerve Injury and Promotes Axonal Growth," *Neuron*, 17:353–361 (1996).

Lee et al., "Comparative Expressed–Sequence–Tag Analysis of Differential Gene Expression Profiles in PC–12 Cells Before and After Nerve Growth Factor Treatment," *Proc. Natl. Acad. Sci. USA*, 92:8303–8307 (1995).

*Primary Examiner*—Marianne P. Allen
*Attorney, Agent, or Firm*—Flehr Hohbach Test Albritton & Herbert LLP; Richard F. Trecartin; Robin M. Silva

[57] ABSTRACT

The present invention includes novel ninjurin proteins, peptides, and nucleic acids, as well as antibodies and pharmaceutical compositions comprising the same. The present invention further includes vectors and host cells comprising those nucleic acid sequences, chimeric protein and peptide molecules comprising the proteins and peptides of the present invention fused to heterologous polypeptide sequences. Also provided herein are antibodies which bind to the proteins and peptides of the present invention and methods for detecting the proteins and peptides of the present invention.

17 Claims, 8 Drawing Sheets

CTGGGCGGCC CGGGCGGCCG CACCATGGAT CCCGGCACCG AGGAGTACGA GCTCAACGGC  60
GACCTGCGCC CTGGCTCTCC CGGTTCCCCC GACGCCTCGC CACCCCGCTG GGGTTTGAGG 120
AACCGGCCCA TCAATGTAAA CCATTACGCC AACAAGAAGA GCGCCGCGGA GAGCATGCTG 180
GACATCGCAC TGCTCATGGC CAACGCGTCG CAGCTCAAGG CCGTGGTGGA GCAGGGCAAT 240
GAGTTCGCCT TCTTCGTGCC CCTCGTGGTG CTCATCTCCA TCTCTCTCGT GCTGCAGATC 300
GGAGTGGGCG TGCTGCTCAT CTTCCTGGTC AAGTATGACC TCAACAACCC AGCCAAGCAC 360
GCCAAGCTGG ACTTCCTTAA CAACCTGGCC ACGGGGCTGG TTTTCATCAT CGTGGTGGTC 420
AACATCTTCA TTACGGCCTT TGGAGTCCAG AAGCCTGTCA TGGACGTGGC ACCCCGGCAG 480
TAGGATGCCC AGAGACCTTG AAGGTATCTG ACCTGCAGCC CAGCTGTCCA GACCCTGCA 540
ACTGCTGTAT CCCCAAGGCA TCCCTCTCCT GTTCACAGCC CAAGGTGGCC TCCGCTGGAC 600
CATGGTCAAG GATGGACTTC CGTCCACCTG TGACTGCTGC GTGGGCGGCC ACCCGAGGCG 660
TGTGGGAACT GGATGCAAAG CCATGAAGAT CAGAACTGGA CAGTTCCACC GAAACCCACG 720
CCCAGAGGAT GATCACTGCC CGCCCAAGGA CATGCAGGAA ATCCATGATT GGACTCGATG 780
AGGGGCCAGA ACTGATCTCT GTCTCAGGAC ATTCCAGAAG GACCAGGATA TGCCCCTCCC 840
TTTGCTGATA CACCAGTGAC CCTACTTCTC ATGGAGCATG CACAGGTCAC CCTGGAGACT 900
GCTCCCTTTG TTGTTTCCTG ACCCAGGGAC CTTGGACAGT CATCAGTACC TGCTGGCTCC 960
AGCCTCAGTG CCTGGGCTTG GCAGTGTCTC TTGGCATCGA GAGGCAGCCA TGCCTGTGGG 1020
GGCTGCAGGT CATCCTGGTA CCTTCTACCA GTAGTGACTT GGGAAGAGCC CCACCCCCA 1080
ACCCAGGGGC TCAGGCCCCA ATTTTCTAAT CAGGAATGAC AATAAAGCTT ATGTCTTCCC 1140
CC                                                              1142

FIG._1A

MDPGTEEYELNGDLRPGSPGSPDASPPRWGLRNRPINVNHYANKKSAAESMLDIALLMAN     60
ASQLKAVVEQGNEFAFFVPLVVLISISLVLQIGVGVLLIFLVKYDLNNPAKHAKLDFLNN   120
LATGLVFIIVVVNIFITAFGVQKPVMDVAPRQ                               152

FIG._1B

```
GCGGCCTGGG CGGCCGCACC ATGGACTCGG GAACCGAGGA GTACGAGCTC AACGGCGGCC   60
TGCCTCCGGG CACACCCGGC TCCCCGGACG CCTCGCCGGC CCGCTGGGGC TGGAGGCACG  120
GGCCCATCAA CGTGAACCAT TACGCCAGCA AGAAGAGCGC AGCCGAGAGC ATGCTGGACA  180
TCGCGCTGCT GATGGCCAAC GCGTCCCAGC TGAAGGCCGT CGTGGAACAG GGCCCCAGCT  240
TCGCCTTCTA TGTGCCCCTG GTGGTCCTCA TCTCCATCTC CCTTGTGCTG CAGATCGGCG  300
TGGGGGTGCT GCTCATCTTC CTTGTCAAGT ACGACCTTAA CAACCCGGAC AAGCACGCCA  360
AGCTGGACTT CCTCAACAAC CTGGCCACGG GCCTGGTGTT CATCATCGTG GTAGTCAACA  420
TCTTCATCAC GGCCTTCGGG GTCCAGAAGC CCTTGATGGA CATGGCACCC AGCAGTAGG   480
ACACCCAGGA CCCTGGATGC TGCCTGCCCT GCAACTCAGC TGCCCGACCC CAGGAGTCGC  540
CATACCTGTG AGGTGTCCAC CTCCCTGCAC ATGGCACTAC CCAGACTGCC AGAGCCCAGG  600
CTGGCCTCAT CTGCACCATG TCCCCGGACC AGCCCTTGCT CTGACTGCGG CCAAGCACCA  660
CGCAGGAGGC CACTCTTGTC TCTCASCAGC TGTTCCCAGG AGGCAGCTCC CTCCTGGCAC  720
ATGGGGCTG GCACAATAGC CCAGAGGGTC AGAACTGGAC AGCTGCAGAG ACCTGTGCCC  780
AGAGAAGGGT CTCGACCCAC TCAAGGACAC ACAGCAGGTC CGTGGATGGG CTGGATGAGT  840
GACCAGGGCC AGCCTCTGTC TCAGGACATT CCAGAAGGAC AAGGAGATGT CTCTCCCTCT  900
CCCAAAGCAC CAGCGTCCCT GCCTCCCGTG GGCCCTGTCC GGGTTGCCCC TGGTGACCCC  960
AGCCTCTGTC CACTTCCTAA CCCAGGGACC CTGCACAGCC AGAACTGCCT TTGGCCCTAC 1020
GGATGGCCAC TGGCTCTGGT CTAAAGTGCC TGGGCTTGGT GGCCATCAAG AGGGAGCCAG 1080
TCAGGCCTGT GAGGGCCGTA GACCTTGTAT ATACCCTGCA CCAGCAGTGA CCGGGCAGAG 1140
CCCAACCCCC TCCACGGGGG TCCCAGCACC CACTTTTCTA ATCATGAATG AACAATAAAG 1200
CCCACGCTCT TTGTCAGGCA AAAAAAAAAA AAAAA                            1235
```

FIG.\_2A

```
MDSGTEEYELNGGLPPGTPGSPDASPARWGWRHGPINVNHYASKKSAAESMLDIALLMAN   60
ASQLKAVVEQGPSFAFYVPLVVLISISLVLQIGVGVLLIFLVKYDLNNPDKHAKLDFLNN  120
LATGLVFIIVVVNIFITAFGVQKPLMDMAPQQ                              152
```

FIG.\_2B

```
CCCACGCAGT CTGTTCCCGG CACCCGGTGC GTGTGAAGGG ACTTGAGGGC AGCGAGATGG    60
AATCAGCAAG AGAAAACATC GACCTTCAAC CTGGAAGCTC CGACCCCAGG AGCCAGCCCA   120
TCAACCTGAA CCATTACGCC ACCAAGAAGA GCGTGGCGGA GAGCATGCTG GACGTGGCCC   180
TGTTCATGTC CAACGCCATG CGGCTGAAGG CGGTGCTGGA GCAGGGACCA TCCTCTCATT   240
ACTACACCAC CCTGGTCACC CTCATCAGCC TCTCTCTGCT CCTGCAGGTG GTCATCGGTG   300
TCCTGCTCGT GGTCATTGCA CGGCTGAACC TGAATGAGGT AGAAAAGCAG TGGCGACTCA   360
ACCAGCTCAA CAACGCAGCC ACCATCTTGG TCTTCTTCAC TGTGGTCATC AATGTTTTCA   420
TTACAGCCTT CGGGGCACAT AAAACAGGGT TCCTGGCTGC CAGGGCCTCA AGGAATCCTC   480
TCTGAATGCA GCCTGGGACC CAGGTTCTGG GCCTGGAACT TCTGCCTCCT TCCTCCGTGA   540
TCTGCCAGGC TCGTGGGCAC TTTCCACAGC CCAGGAGAGC TTCTGAAAGG ACAGTATAGC   600
TGCCCTTGCT CCCTACCCAC AGCACCTGAG TTAAAAAGTG ATTTTATGT TATTGGTCTA   660
AGGGACTTCC ATCTTGGTCT GAAGTCCTGA GCTCAGACGC AGGTACTGCC AGCCATACCT   720
TCCTGGTAGC ATCTGCTGGA CCTAAGTAAG CATGTCTGT CTAAGGCCAA GTCTGCCCGG   780
CTTAAGGATG CTGGTTCTGA CTCTACCCCA CTGCTTCCTT CTGCTCCAGG CCTCAATTTT   840
CCCTTCTTGT AAAATGGAAT CTATATCTAT AAAGGTTTCT TCAAATCCAA AAAAAAAAA   900
AAAAAAA                                                             907
```

FIG._3A

```
MESARENIDLQPGSSDPRSQPINLNHYATKKSVAESMLDVALFMSNAMRLKAVLEQGPSS    60
HYYTTLVTLISLSLLLQVVIGVLLVVIARLNLNEVEKQWRLNQLNNAATILVFFTVVINV   120
FITAFGAHKTGFLAARASRNPL                                         142
```

FIG._3B

```
CCACCCGGGC AGGTCCACGC TCAGCCTTGT TTTGTTTTGT TTTGTTTTGT TTTTGAAACC    60
GGGTCTTGCT GTGTCTTGAT CACAGCTCAC TGCAGTCTCA ACCTCCCAGG CTCAAGCGAG   120
CCTTCTGCCT CAGCCTCCCA GGTAGGCTGG ACCACAGCTA TATGCCATCA TGCCAGCTAA   180
TTTTTTTATT TTTGGTAGAC ACGGGGTCTT GCTATGCTGC CCAGGCTGGT CTCAAACTCC   240
CTGGGCTCAC GTGATCCTCC TGTCTCGGCC TCCCAAAGTG CTGGGATTAC AGGTATGAAC   300
CACTGTGCCT GGCCCCACCC TGCACTTTGA AAGAGCACAG AGTGGGGTCA GGGCCTGGCC   360
TGTGGGCATT AGGGCAGGTG TTTCACCGGG TTCTTGTTGA CCCATGCCAT GAGATGGCCT   420
CAGTCATGCC AGTCCTACCT TCTGGGCCCA GGGTCCCCCT CATGGCTGCG TAACCTTGGG   480
CAAGTGGCTG AACCTCCCGG GCCTCACTTA TAAAACAAGC ATCATAATAG AACTGCAGCT   540
TGTGGCAGGA ATCACTAGAT TAAGGCACGC AAAGGGCTCA GTGCATTTGC CCAAACCTGG   600
CCTTTGGTTG ACGTCCATAG CTTCAATTCG TATAAGGAAA ATATGGGGC TACAGAAGGT   660
GGGGTCATAG ACCGTGGGGT TGCCCAAGCC AGGGGCGCTG TTGTCCATGT TTCAGCAAAA   720
CAGATGTATT TTTCTCTGGG CGACAAAACT CATCCTAAAT GCGACTGAGA GCCCTGTAAT   780
GTCCCAGGAC AGCTTGACCG CTGGGGTGGG TCCCCTTCCA CTGTCCCAGG CTGGGGCGCT   840
GCGTCTGGGC TGCCCTTGGC ACCATCCACT CCTCTCTCGC CCACAGTCAA GTACGACCTT   900
AACAACCCGG CCAAGCACGC CAAGCTGGAC TTCCTCAACA ACCTGGCCAC GGGCCTGGTG   960
TTCATCATCG TGGTAGTCAA CATCTTCATC ACGGCCTTCG GGTCCAGAA GCCCTTGATG  1020
GACATGGCAC CCCAGCAGTA GGACACCCAG GTGAGCTGGG AGATGGGGCG CGAGGCCTGC  1080
AGTCCTGGGG TTGCTCGCTG TTGGAGGCTC TTGCAGTGTG GTGAGTCCCT GGCCGGCCAG  1140
CCTTGGACAC CTTCCTAGGC CATGGGCATC CTCGTCCACA CCTACAAGGC CAATGCCTGG  1200
CCACTGCCTT GAGGCCAGCC CTGCCACTGG TGCTGGCCAC CTGGGGTCCT GTGGTCACAG  1260
TGTTTAGATG GAATGTGTGT AGGAGCCACC ATTTGAACAT CCTGGAGAAC TCACTTAAAC  1320
GTAAGATTTC TATACATTCA GAATGTCTGT CCGATAAAAA AAAAAAAAAA AAAA        1374
```

FIG._4

```
GGCACGAGCG TGGCTCAAAC GACCGCCGCT AAGAACAAAA CGTTGGCTTT GGCTTCGTTG    60
CAAAGCAGCC GCTCGGTGGC CGTACAACGC TTCATCTCTC CGAGCCTCGG TTTCCTCATC   120
TCCAGCCCTA AAATGACGAC ACGCCCCACA GGTCTTGGGA GGATTAAGTG AGGGGACATG   180
AGGTGGTCAT CGGTGTCCTG CTCGTGGTCA TTGGTGAGGA GCCCAGCCTG CAGTCAGACC   240
TTCTGCCTCG GCACCCGTGG CTGGCAGAAA GGCCCCACGT GTCCCTGGG CCACCCTGCA   300
TTGGCACAGG CAGCTTTGCA ACCACACGCT GACCTGCAGT GAGCCCTCCG CTAACAGAGG   360
CCCAAAGACC AACTTCCACC CCGCGAGGGC AGGCGCCCTG TCCTGTCTCC TGCACGGCTG   420
AACCTGAATG AGGTAGAAAA GCAGTGGCGA CTCAACCAGC TCAACAACGC AGCCACCATC   480
TTGGTCTTCT TCACTGTGGT CATCAATGTT TTCATTACAG CCTTCGGGGC ACATAAAACA   540
GGGTTCCTGG CTGCCAGGGC CTCAAGGAAT CCTCTCTGAA TGCAGCCTGG GACCCAGGTT   600
CTGGGCCTGG AACTTCTGCC TCCTTCCTCC GTGATCTGCC AGGCTCGTGG GCACTTTCCA   660
CAGCCCAGGA GAGCTTCTGA AAGGACAGTA TAGCTGCCCT TGCTCCCTAC CCACAGCACC   720
TGAGTTAAAA AGTGATTTTT ATGTTATTGG TCTAAGGGAC TTCCATCTTG GTCTGAAGTC   780
CTGAGCTCAG ACGCAGGTAC TGCCAGCCAT ACCTTCCTGG TAGCATCTGC TGGACCTAAG   840
TAAGGCATGT CTGTCTAAGG CCAAGTCTGC CCGGCTTAAG GATGCTGGTT CTGACTCTAC   900
CCCACTGCTT CCTTCTGCTC CAGGCCTCAA TTTTCCCTTC TTGTAAAATG GAATCTATAT   960
CTATAAAGGT TTCTTCAAAT CCAAAAAAAA AAAAAAAAA A                       1001
```

FIG._5

```
ATCTCTCCGA GCCTCGGTTT CCTCATCTCC AGCCCTAAAA TGACGACACG CCCCACAGGT    60
CTTGGGAGGA TTAAGTGAGG GGACATGAGC CTGGAAGCTC CGACCCCAGG AGCCAGCCCA   120
TCAACCTGAA CCATTACGCC ACCAAGAAGA GCGTGGCGGA GAGCATGCTG ACGTGGCCC    180
TGTTCATGTC CAACGCCATG CGGCTGAAGG CGGTGCTGGA GCAGGGACCA TCCTCTCATT   240
ACTACACCAC CCTGGTCACC CTCATCAGCC TCTCTCTGCT CCTGCAGGTG GTCATCGGTG   300
TCCTGCTCGT GGTCATTGCA CGGCTGAACC TGAATGAGGT AGAAAAGCAG TGGCGACTCA   360
ACCAGCTCAA CAACGCAGCC ACCATCTTGG TCTTCTTCAC TGTGGTCATC AATGTTTTCA   420
TTACAGCCTT CGGGGCACAT AAAACAGGGT TCCTGGCTGC CAGGGCCTCA AGGAATCCTC   480
TCTGAATGCA GCCTGGGACC CAGGTTCTGG GCCTGGAACT TCTGCCTCCT TCCTCCGTGA   540
TCTGCCAGGC TCGTGGGCAC TTTCCACAGC CCAGGAGAGC TTCTGAAAGG ACAGTATAGC   600
TGCCCTTGCT CCCTACCCAC AGCACCTGAG TTAAAAAGTG ATTTTTATGT TATTGGTCTA   660
AGGGACTTCC ATCTTGGTCT GAAGTCCTGA GCTCAGACGC AGGTACTGCC AGCCATACCT   720
TCCTGGTAGC ATCTGCTGGA CCTAAGTAAG GCATGTCTGT CTAAGGCCAA GTCTGCCCGG   780
CTTAAGGATG CTGGTTCTGA CTCTACCCCA CTGCTTCCTT CTGCTCCAGG CCTCAATTTT   840
CCCTTCTTGT AAAATGGAAT CTATATCTAT AAAGGTTTCT TCAAATCCAA AAAAAAAAA   900
AAAAAAA                                                             907
```

FIG._6

```
      M D S G T E E Y E L N G X L X P G X P G S P D A S P X R W G X R X X P I N V N H   Majority
                    10                  20                  30                  40
   1  M D P G T E E Y E L N G D L R P G S P G S P D A S P P R W G L R N R P I N V N H   ratninjurin
   1  M D S G T E E Y E L N G G L P P G T P G S P D A S P A R W G W R H G P I N V N H   T84142(HUMAN NINJURIN)
   1  M E S A R E N I D L Q - - - - - - P G S S D P - - - - - R S Q P I N L N H         H91351(HUMAN NINJURIN2)

Y A X K K S A A E S M L D I A L L M A N A S Q L K A V V E Q G P S F A F Y V P L   Majority
                    50                  60                  70                  80
  41  Y A N K K S A A E S M L D I A L L M A N A S Q L K A V V E Q G N E F A F F V P L   ratninjurin
  41  Y A S K K S A A E S M L D I A L L M A N A S Q L K A V V E Q G P S F A F Y V P L   T84142(HUMAN NINJURIN)
  27  Y A T K K S V A E S M L D V A L F M S N A M R L K A V L E Q G P S S H Y Y T T L   H91351(HUMAN NINJURIN2)

V V L I S L V L Q I G V G V L L I F L V K Y D L N N P X K H A K L D F L N N       Majority
                    90                 100                 110                 120
  81  V V L I S L V L Q I G V G V L L I F L V K Y D L N N P A K H A K L D F L N N       ratninjurin
  81  V V L I S L V L Q I G V G V L L I F L V K Y D L N N P D K H A K L D F L N N       T84142(HUMAN NINJURIN)
  67  V T L I S L S L L L Q V V I G V L L V V I A R L N L N E V E K Q W R L N Q L N N   H91351(HUMAN NINJURIN2)

L A T G L V F I I V V N I F I T A F G V Q K P - - L M D X A P R Q - -             Majority
                   130                 140                 150
 121  L A T G L V F I I V V N I F I T A F G V Q K P - - V M D V A P R Q .               ratninjurin
 121  L A T G L V F I I V V N I F I T A F G V Q K P - - L M D M A P Q Q .               T84142(HUMAN NINJURIN)
 107  A A T I L V F F T V V I N V F I T A F G A H K T G F L A A R A S R N P L .         H91351(HUMAN NINJURIN2)
```

FIG._7

```
  1           10         20         30         40         50         60         70         80         90        100
MDPGTEEYEL NGDLRPGSPG SPDASPPRWG LRNRPINVNH YANKKSAAES MLDIALLMAN ASQLKAVVEQ GNEFAFFVPL VVLISISLVL QIGVGVLLIF
                                                                           ̳̳̳̳̳̳̳̳̳̳̳̳̳̳̳̳̳̳̳̳̳̳̳̳̳̳̳̳̳̳̳̳̳̳̳̳̳̳̳̳̳̳
                                              (DOUBLE UNDERLINES SHOW THE PUTATIVE
                                                 TRANSMEMBRANE REGION.)
```

FIG._8A

```
1--------------------------30 PEPTIDE 1(-)

16-----------------------------45 PEPTIDE 2(+)

31-----------------------------60 PEPTIDE 3(+)

46-----------------------75 PEPTIDE 4(-)

26------------50 PEPTIDE 5(+)

26-------37 PEPTIDE 6(+)

32------43 PEPTIDE 7(-)

38------50 PEPTIDE 8(-)

(+ AND - SHOWS THE PEPTIDE'S ABILITY TO INHIBIT
               THE NINJURIN-MEDIATED AGGREGATION.)
```

FIG._8B

```
            26-mutations-37  (BOLD CHARACTERS SHOW THE MUTATED RESIDUES)
            |            |
Peptide 9   PPNWG LRNRPIN    mutation effective (= mutation made the peptide less active for
                                                   inhibition of adhesion.)
Peptide 10  PPRAG LRNRPIN    mutation effective
Peptide 11  PPRWA LRNRPIN    mutation not effective (= mutation did not change the activity for
                                                       inhibition of adhesion.)
Peptide 12  PPRWG NRNRPIN    mutation not effective
Peptide 13  PPRWG LNNRPIN    mutation effective
Peptide 14  PPRWG LRLRPIN    mutation made the peptide more active for inhibition of adhesion.
Peptide 15  PPRWG LRNNPIN    mutation effective
```

FIG._8C

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: unknown
      (D) TOPOLOGY: unknown (ii) MOLECULE TYPE: protein (xi) SEQUENCE DESCRIPTION: SEQ ID NO:1:

Asp Xaa Asn Asp Asn
1               5

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:2:

Lys Tyr Ser Phe Asn Tyr Asp Gly Ser Glu
1               5                   10

(2) INFORMATION FOR SEQ ID NO:3:

(i) SEQUENCE CHARACTERISTICS:
        (A) LENGTH: 1142 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

```
CTGGGCGGCC CGGGCGGCCG CACCATGGAT CCCGGCACCG AGGAGTACGA GCTCAACGGC      60
GACCTGCGCC CTGGCTCTCC CGGTTCCCCC GACGCCTCGC CACCCCGCTG GGGTTTGAGG     120
AACCGGCCCA TCAATGTAAA CCATTACGCC AACAAGAAGA GCGCCGCGGA GAGCATGCTG     180
GACATCGCAC TGCTCATGGC CAACGCGTCG CAGCTCAAGG CCGTGGTGGA GCAGGGCAAT     240
GAGTTCGCCT TCTTCGTGCC CCTCGTGGTG CTCATCTCCA TCTCTCTCGT GCTGCAGATC     300
GGAGTGGGCG TGCTGCTCAT CTTCCTGGTC AAGTATGACC TCAACAACCC AGCCAAGCAC     360
GCCAAGCTGG ACTTCCTTAA CAACCTGGCC ACGGGGCTGG TTTTCATCAT CGTGGTGGTC     420
AACATCTTCA TTACGGCCTT TGGAGTCCAG AAGCCTGTCA TGGACGTGGC ACCCCGGCAG     480
TAGGATGCCC AGAGACCTTG AAGGTATCTG ACCTGCAGCC CAGCTGTCCA GACCCCTGCA     540
ACTGCTGTAT CCCCAAGGCA TCCCTCTCCT GTTCACAGCC CAAGGTGGCC TCCGCTGGAC     600
CATGGTCAAG GATGGACTTC CGTCCACCTG TGACTGCTGC GTGGGCGGCC ACCCGAGGCG     660
TGTGGGAACT GGATGCAAAG CCATGAAGAT CAGAACTGGA CAGTTCCACC GAAACCCACG     720
CCCAGAGGAT GATCACTGCC CGCCCAAGGA CATGCAGGAA ATCCATGATT GGACTCGATG     780
AGGGGCCAGA ACTGATCTCT GTCTCAGGAC ATTCCAGAAG GACCAGGATA TGCCCCTCCC     840
TTTGCTGATA CACCAGTGAC CCTACTTCTC ATGGAGCATG CACAGGTCAC CCTGGAGACT     900
GCTCCCTTTG TTGTTTCCTG ACCCAGGGAC CTTGGACAGT CATCAGTACC TGCTGGCTCC     960
AGCCTCAGTG CCTGGGCTTG GCAGTGTCTC TTGGCATCGA GAGGCAGCCA TGCCTGTGGG    1020
GGCTGCAGGT CATCCTGGTA CCTTCTACCA GTAGTGACTT GGGAAGAGCC CCACCCCCCA    1080
ACCCAGGGGC TCAGGCCCCA ATTTTCTAAT CAGGAATGAC AATAAAGCTT ATGTCTTCCC    1140
CC                                                                   1142
```

(2) INFORMATION FOR SEQ ID NO:4:

(i) SEQUENCE CHARACTERISTICS:
    (A) LENGTH: 152 amino acids
    (B) TYPE: amino acid
    (C) STRANDEDNESS: unknown
    (D) TOPOLOGY: unknown (ii) MOLECULE TYPE: protein (xi) SEQUENCE DESCRIPTION: SEQ ID NO:4:

```
Met Asp Pro Gly Thr Glu Tyr Glu Leu Asn Gly Asp Leu Arg Pro
1               5                   10                  15

Gly Ser Pro Gly Ser Pro Asp Ala Ser Pro Pro Arg Trp Gly Leu Arg
            20                  25                  30

Asn Arg Pro Ile Asn Val Asn His Tyr Ala Asn Lys Lys Ser Ala Ala
            35                  40                  45

Glu Ser Met Leu Asp Ile Ala Leu Leu Met Ala Asn Ala Ser Gln Leu
50                      55                      60

Lys Ala Val Val Glu Gln Gly Asn Glu Phe Ala Phe Phe Val Pro Leu
65                  70                      75                  80

Val Val Leu Ile Ser Ile Ser Leu Val Leu Gln Ile Gly Val Gly Val
                85                  90                      95

Leu Leu Ile Phe Leu Val Lys Tyr Asp Leu Asn Asn Pro Ala Lys His
                100                 105                 110

Ala Lys Leu Asp Phe Leu Asn Asn Leu Ala Thr Gly Leu Val Phe Ile
            115                 120                 125

Ile Val Val Asn Ile Phe Ile Thr Ala Phe Gly Val Gln Lys Pro
            130                 135                 140

Val Met Asp Val Ala Pro Arg Gln
145                 150
```

(2) INFORMATION FOR SEQ ID NO:5:

(i) SEQUENCE CHARACTERISTICS:
        (A) LENGTH: 1235 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:5:

```
GCGGCCTGGG CGGCCGCACC ATGGACTCGG GAACCGAGGA GTACGAGCTC AACGGCGGCC    60

TGCCTCCGGG CACACCCGGC TCCCCGGACG CCTCGCCGGC CCGCTGGGGC TGGAGGCACG   120

GGCCCATCAA CGTGAACCAT TACGCCAGCA AGAAGAGCGC AGCCGAGAGC ATGCTGGACA   180

TCGCGCTGCT GATGGCCAAC GCGTCCCAGC TGAAGGCCGT CGTGGAACAG GGCCCCAGCT   240

TCGCCTTCTA TGTGCCCCTG GTGGTCCTCA TCTCCATCTC CCTTGTGCTG CAGATCGGCG   300

TGGGGGTGCT GCTCATCTTC CTTGTCAAGT ACGACCTTAA CAACCCGGAC AAGCACGCCA   360

AGCTGGACTT CCTCAACAAC CTGGCCACGG GCCTGGTGTT CATCATCGTG GTAGTCAACA   420

TCTTCATCAC GGCCTTCGGG GTCCAGAAGC CCTTGATGGA CATGGCACCC CAGCAGTAGG   480

ACACCCAGGA CCCTGGATGC TGCCTGCCCT GCAACTCAGC TGCCCGACCC CAGGAGTCGC   540

CATACCTGTG AGGTGTCCAC CTCCCTGCAC ATGGCACTAC CCAGACTGCC AGAGCCCAGG   600

CTGGCCTCAT CTGCACCATG TCCCCGGACC AGCCCTTGCT CTGACTGCGG CCAAGCACCA   660

CGCAGGAGGC CACTCTTGTC TCTCASCAGC TGTTCCCAGG AGGCAGCTCC CTCCTGGCAC   720

ATGGGGGCTG GCACAATAGC CCAGAGGGTC AGAACTGGAC AGCTGCAGAG ACCTGTGCCC   780
```

```
AGAGAAGGGT CTCGACCCAC TCAAGGACAC ACAGCAGGTC CGTGGATGGG CTGGATGAGT     840

GACCAGGGCC AGCCTCTGTC TCAGGACATT CCAGAAGGAC AAGGAGATGT CTCTCCCTCT     900

CCCAAAGCAC CAGCGTCCCT GCCTCCCGTG GGCCCTGTCC GGGTTGCCCC TGGTGACCCC     960

AGCCTCTGTC CACTTCCTAA CCCAGGGACC CTGCACAGCC AGAACTGCCT TTGGCCCTAC    1020

GGATGGCCAC TGGCTCTGGT CTAAAGTGCC TGGGCTTGGT GGCCATCAAG AGGGAGCCAG    1080

TCAGGCCTGT GAGGGCCGTA GACCTTGTAT ATACCCTGCA CCAGCAGTGA CCGGGCAGAG    1140

CCCAACCCCC TCCACGGGGG TCCCAGCACC CACTTTTCTA ATCATGAATG AACAATAAAG    1200

CCCACGCTCT TTGTCAGGCA AAAAAAAAAA AAAAA                               1235

(2) INFORMATION FOR SEQ ID NO:6:

(i) SEQUENCE CHARACTERISTICS:
        (A) LENGTH: 152 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:6:

Met Asp Ser Gly Thr Glu Glu Tyr Glu Leu Asn Gly Gly Leu Pro Pro
1               5                   10                  15

Gly Thr Pro Gly Ser Pro Asp Ala Ser Pro Ala Arg Trp Gly Trp Arg
                20                  25                  30

His Gly Pro Ile Asn Val Asn His Tyr Ala Ser Lys Lys Ser Ala Ala
            35                  40                  45

Glu Ser Met Leu Asp Ile Ala Leu Leu Met Ala Asn Ala Ser Gln Leu
        50                  55                  60

Lys Ala Val Val Glu Gln Gly Pro Ser Phe Ala Phe Tyr Val Pro Leu
65                  70                  75                  80

Val Val Leu Ile Ser Ile Ser Leu Val Leu Gln Ile Gly Val Gly Val
                85                  90                  95

Leu Leu Ile Phe Leu Val Lys Tyr Asp Leu Asn Asn Pro Asp Lys His
            100                 105                 110

Ala Lys Leu Asp Phe Leu Asn Asn Leu Ala Thr Gly Leu Val Phe Ile
        115                 120                 125

Ile Val Val Asn Ile Phe Ile Thr Ala Phe Gly Val Gln Lys Pro
    130                 135                 140

Leu Met Asp Met Ala Pro Gln Gln
145                 150

(2) INFORMATION FOR SEQ ID NO:7:

(i) SEQUENCE CHARACTERISTICS:
        (A) LENGTH: 907 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:7:

CCCACGCAGT CTGTTCCCGG CACCCGGTGC GTGTGAAGGG ACTTGAGGGC AGCGAGATGG      60

AATCAGCAAG AGAAAACATC GACCTTCAAC CTGGAAGCTC CGACCCCAGG AGCCAGCCCA     120

TCAACCTGAA CCATTACGCC ACCAAGAAGA GCGTGGCGGA GAGCATGCTG ACGTGGCCC      180

TGTTCATGTC CAACGCCATG CGGCTGAAGG CGGTGCTGGA GCAGGGACCA TCCTCTCATT     240
```

```
ACTACACCAC CCTGGTCACC CTCATCAGCC TCTCTCTGCT CCTGCAGGTG GTCATCGGTG     300

TCCTGCTCGT GGTCATTGCA CGGCTGAACC TGAATGAGGT AGAAAAGCAG TGGCGACTCA     360

ACCAGCTCAA CAACGCAGCC ACCATCTTGG TCTTCTTCAC TGTGGTCATC AATGTTTTCA     420

TTACAGCCTT CGGGGCACAT AAAACAGGGT TCCTGGCTGC CAGGGCCTCA AGGAATCCTC     480

TCTGAATGCA GCCTGGGACC CAGGTTCTGG GCCTGGAACT TCTGCCTCCT TCCTCCGTGA     540

TCTGCCAGGC TCGTGGGCAC TTTCCACAGC CCAGGAGAGC TTCTGAAAGG ACAGTATAGC     600

TGCCCTTGCT CCCTACCCAC AGCACCTGAG TTAAAAAGTG ATTTTTATGT TATTGGTCTA     660

AGGGACTTCC ATCTTGGTCT GAAGTCCTGA GCTCAGACGC AGGTACTGCC AGCCATACCT     720

TCCTGGTAGC ATCTGCTGGA CCTAAGTAAG GCATGTCTGT CTAAGGCCAA GTCTGCCCGG     780

CTTAAGGATG CTGGTTCTGA CTCTACCCCA CTGCTTCCTT CTGCTCCAGG CCTCAATTTT     840

CCCTTCTTGT AAAATGGAAT CTATATCTAT AAAGGTTTCT TCAAATCCAA AAAAAAAAA     900

AAAAAAA                                                               907
```

(2) INFORMATION FOR SEQ ID NO:8:

(i) SEQUENCE CHARACTERISTICS:
        (A) LENGTH: 142 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:8:

```
Met Glu Ser Ala Arg Glu Asn Ile Asp Leu Gln Pro Gly Ser Ser Asp
1               5                   10                  15

Pro Arg Ser Gln Pro Ile Asn Leu Asn His Tyr Ala Thr Lys Lys Ser
            20                  25                  30

Val Ala Glu Ser Met Leu Asp Val Ala Leu Phe Met Ser Asn Ala Met
        35                  40                  45

Arg Leu Lys Ala Val Leu Glu Gln Gly Pro Ser Ser His Tyr Tyr Thr
    50                  55                  60

Thr Leu Val Thr Leu Ile Ser Leu Ser Leu Leu Leu Gln Val Val Ile
65                  70                  75                  80

Gly Val Leu Leu Val Val Ile Ala Arg Leu Asn Leu Asn Glu Val Glu
                85                  90                  95

Lys Gln Trp Arg Leu Asn Gln Leu Asn Asn Ala Ala Thr Ile Leu Val
            100                 105                 110

Phe Phe Thr Val Val Ile Asn Val Phe Ile Thr Ala Phe Gly Ala His
        115                 120                 125

Lys Thr Gly Phe Leu Ala Ala Arg Ala Ser Arg Asn Pro Leu
    130                 135                 140
```

(2) INFORMATION FOR SEQ ID NO:9:

(i) SEQUENCE CHARACTERISTICS:
        (A) LENGTH: 1374 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:9:

```
CCACCCGGGC AGGTCCACGC TCAGCCTTGT TTTGTTTTGT TTTGTTTTGT TTTTGAAACC     60
```

```
GGGTCTTGCT GTGTCTTGAT CACAGCTCAC TGCAGTCTCA ACCTCCCAGG CTCAAGCGAG      120

CCTTCTGCCT CAGCCTCCCA GGTAGGCTGG ACCACAGCTA TATGCCATCA TGCCAGCTAA      180

TTTTTTTATT TTTGGTAGAC ACGGGGTCTT GCTATGCTGC CCAGGCTGGT CTCAAACTCC      240

CTGGGCTCAC GTGATCCTCC TGTCTCGGCC TCCCAAAGTG CTGGGATTAC AGGTATGAAC      300

CACTGTGCCT GGCCCCACCC TGCACTTTGA AAGAGCACAG AGTGGGGTCA GGGCCTGGCC      360

TGTGGGCATT AGGGCAGGTG TTTCACCGGG TTCTTGTTGA CCCATGCCAT GAGATGGCCT      420

CAGTCATGCC AGTCCTACCT TCTGGGCCCA GGGTCCCCCT CATGGCTGCG TAACCTTGGG      480

CAAGTGGCTG AACCTCCCGG GCCTCACTTA TAAAACAAGC ATCATAATAG AACTGCAGCT      540

TGTGGCAGGA ATCACTAGAT TAAGGCACGC AAAGGGCTCA GTGCATTTGC CCAAACCTGG      600

CCTTTGGTTG ACGTCCATAG CTTCAATTCG TATAAGGAAA ATATGGGGGC TACAGAAGGT      660

GGGGTCATAG ACCGTGGGGT TGCCCAAGCC AGGGGCGCTG TTGTCCATGT TTCAGCAAAA      720

CAGATGTATT TTTCTCTGGG CGACAAAACT CATCCTAAAT GCGACTGAGA GCCCTGTAAT      780

GTCCCAGGAC AGCTTGACCG CTGGGGTGGG TCCCCTTCCA CTGTCCCAGG CTGGGGCGCT      840

GCGTCTGGGC TGCCCTTGGC ACCATCCACT CCTCTCTCGC CCACAGTCAA GTACGACCTT      900

AACAACCCGG CCAAGCACGC CAAGCTGGAC TTCCTCAACA ACCTGGCCAC GGGCCTGGTG      960

TTCATCATCG TGGTAGTCAA CATCTTCATC ACGGCCTTCG GGGTCCAGAA GCCCTTGATG      1020

GACATGGCAC CCCAGCAGTA GGACACCCAG GTGAGCTGGG AGATGGGGCG CGAGGCCTGC      1080

AGTCCTGGGG TTGCTCGCTG TTGGAGGCTC TTGCAGTGTG GTGAGTCCCT GGCCGGCCAG      1140

CCTTGGACAC CTTCCTAGGC CATGGGCATC CTCGTCCACA CCTACAAGGC CAATGCCTGG      1200

CCACTGCCTT GAGGCCAGCC CTGCCACTGG TGCTGGCCAC CTGGGTCCT GTGGTCACAG      1260

TGTTTAGATG GAATGTGTGT AGGAGCCACC ATTTGAACAT CCTGGAGAAC TCACTTAAAC      1320

GTAAGATTTC TATACATTCA GAATGTCTGT CCGATAAAAA AAAAAAAAAA AAAA           1374

(2) INFORMATION FOR SEQ ID NO:10:

(i) SEQUENCE CHARACTERISTICS:
            (A) LENGTH: 1001 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:10:

GGCACGAGCG TGGCTCAAAC GACCGCCGCT AAGAACAAAA CGTTGGCTTT GGCTTCGTTG       60

CAAAGCAGCC GCTCGGTGGC CGTACAACGC TTCATCTCTC CGAGCCTCGG TTTCCTCATC      120

TCCAGCCCTA AAATGACGAC ACGCCCCACA GGTCTTGGGA GGATTAAGTG AGGGGACATG      180

AGGTGGTCAT CGGTGTCCTG CTCGTGGTCA TTGGTGAGGA GCCCAGCCTG CAGTCAGACC      240

TTCTGCCTCG GCACCCGTGG CTGGCAGAAA GGCCCCACGT GTCCCTGGG CCACCCTGCA      300

TTGGCACAGG CAGCTTTGCA ACCACACGCT GACCTGCAGT GAGCCCTCCG CTAACAGAGG      360

CCCAAAGACC AACTTCCACC CCGCGAGGGC AGGCGCCCTG TCCTGTCTCC TGCACGGCTG      420

AACCTGAATG AGGTAGAAAA GCAGTGGCGA CTCAACCAGC TCAACAACGC AGCCACCATC      480

TTGGTCTTCT TCACTGTGGT CATCAATGTT TTCATTACAG CCTTCGGGGC ACATAAAACA      540

GGGTTCCTGG CTGCCAGGGC CTCAAGGAAT CCTCTCTGAA TGCAGCCTGG GACCCAGGTT      600

CTGGGCCTGG AACTTCTGCC TCCTTCCTCC GTGATCTGCC AGGCTCGTGG GCACTTTCCA      660
```

CAGCCCAGGA GAGCTTCTGA AAGGACAGTA TAGCTGCCCT TGCTCCCTAC CCACAGCACC    720

TGAGTTAAAA AGTGATTTTT ATGTTATTGG TCTAAGGGAC TTCCATCTTG GTCTGAAGTC    780

CTGAGCTCAG ACGCAGGTAC TGCCAGCCAT ACCTTCCTGG TAGCATCTGC TGGACCTAAG    840

TAAGGCATGT CTGTCTAAGG CCAAGTCTGC CCGGCTTAAG GATGCTGGTT CTGACTCTAC    900

CCCACTGCTT CCTTCTGCTC CAGGCCTCAA TTTTCCCTTC TTGTAAAATG GAATCTATAT    960

CTATAAAGGT TTCTTCAAAT CCAAAAAAAA AAAAAAAAA A                        1001

(2) INFORMATION FOR SEQ ID NO:11:

(i) SEQUENCE CHARACTERISTICS:
        (A) LENGTH: 907 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:11:

ATCTCTCCGA GCCTCGGTTT CCTCATCTCC AGCCCTAAAA TGACGACACG CCCCACAGGT     60

CTTGGGAGGA TTAAGTGAGG GGACATGAGC CTGGAAGCTC CGACCCCAGG AGCCAGCCCA    120

TCAACCTGAA CCATTACGCC ACCAAGAAGA GCGTGGCGGA GAGCATGCTG GACGTGGCCC    180

TGTTCATGTC CAACGCCATG CGGCTGAAGG CGGTGCTGGA GCAGGGACCA TCCTCTCATT    240

ACTACACCAC CCTGGTCACC CTCATCAGCC TCTCTCTGCT CCTGCAGGTG GTCATCGGTG    300

TCCTGCTCGT GGTCATTGCA CGGCTGAACC TGAATGAGGT AGAAAAGCAG TGGCGACTCA    360

ACCAGCTCAA CAACGCAGCC ACCATCTTGG TCTTCTTCAC TGTGGTCATC AATGTTTTCA    420

TTACAGCCTT CGGGGCACAT AAAACAGGGT TCCTGGCTGC CAGGGCCTCA AGGAATCCTC    480

TCTGAATGCA GCCTGGGACC CAGGTTCTGG GCCTGGAACT TCTGCCTCCT TCCTCCGTGA    540

TCTGCCAGGC TCGTGGGCAC TTTTCCACAGC CCAGGAGAGC TTCTGAAAGG ACAGTATAGC    600

TGCCCTTGCT CCCTACCCAC AGCACCTGAG TTAAAAAGTG ATTTTTATGT TATTGGTCTA    660

AGGGACTTCC ATCTTGGTCT GAAGTCCTGA GCTCAGACGC AGGTACTGCC AGCCATACCT    720

TCCTGGTAGC ATCTGCTGGA CCTAAGTAAG GCATGTCTGT CTAAGGCCAA GTCTGCCCGG    780

CTTAAGGATG CTGGTTCTGA CTCTACCCCA CTGCTTCCTT CTGCTCCAGG CCTCAATTTT    840

CCCTTCTTGT AAAATGGAAT CTATATCTAT AAAGGTTTCT TCAAATCCAA AAAAAAAAA    900

AAAAAAA                                                              907

(2) INFORMATION FOR SEQ ID NO:12:

(i) SEQUENCE CHARACTERISTICS:
        (A) LENGTH: 152 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:12:

Met Asp Ser Gly Thr Glu Glu Tyr Glu Leu Asn Gly Xaa Leu Xaa Pro
1               5                   10                  15

Gly Xaa Pro Gly Ser Pro Asp Ala Ser Pro Xaa Arg Trp Gly Xaa Arg
            20                  25                  30

Xaa Xaa Pro Ile Asn Val Asn His Tyr Ala Xaa Lys Lys Ser Ala Ala
        35                  40                  45

```
Glu Ser Met Leu Asp Ile Ala Leu Leu Met Ala Asn Ala Ser Gln Leu
         50                  55                  60

Lys Ala Val Val Glu Gln Gly Pro Ser Phe Ala Phe Tyr Val Pro Leu
 65                  70                  75                  80

Val Val Leu Ile Ser Ile Ser Leu Val Leu Gln Ile Gly Val Gly Val
                 85                  90                  95

Leu Leu Ile Phe Leu Val Lys Tyr Asp Leu Asn Asn Pro Xaa Lys His
            100                 105                 110

Ala Lys Leu Asp Phe Leu Asn Asn Leu Ala Thr Gly Leu Val Phe Ile
            115                 120                 125

Ile Val Val Asn Ile Phe Ile Thr Ala Phe Gly Val Gln Lys Pro
            130                 135                 140

Leu Met Asp Xaa Ala Pro Arg Gln
145                 150
```

(2) INFORMATION FOR SEQ ID NO:13:

(i) SEQUENCE CHARACTERISTICS:
        (A) LENGTH: 100 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:13:

```
Met Asp Pro Gly Thr Glu Tyr Glu Leu Asn Gly Asp Leu Arg Pro
 1               5                  10                  15

Gly Ser Pro Gly Ser Pro Asp Ala Ser Pro Pro Arg Trp Gly Leu Arg
                 20                  25                  30

Asn Arg Pro Ile Asn Val Asn His Tyr Ala Asn Lys Lys Ser Ala Ala
             35                  40                  45

Glu Ser Met Leu Asp Ile Ala Leu Leu Met Ala Asn Ala Ser Gln Leu
         50                  55                  60

Lys Ala Val Val Glu Gln Gly Asn Glu Phe Ala Phe Phe Val Pro Leu
 65                  70                  75                  80

Val Val Leu Ile Ser Ile Ser Leu Val Leu Gln Ile Gly Val Gly Val
                 85                  90                  95

Leu Leu Ile Phe
            100
```

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:14:

```
Pro Pro Asn Trp Gly Leu Arg Asn Arg Pro Ile Asn
 1               5                  10
```

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS: unknown (D) TOPOLOGY: unknown (ii) MOLECULE TYPE: protein (xi) SEQUENCE DESCRIPTION: SEQ ID NO:15:

Pro Pro Arg Ala Gly Leu Arg Asn Arg Pro Ile Asn
1               5                   10

(2) INFORMATION FOR SEQ ID NO:16:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:16:

Pro Pro Arg Trp Ala Leu Arg Asn Arg Pro Ile Asn
1               5                   10

(2) INFORMATION FOR SEQ ID NO:17:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:17:

Pro Pro Arg Trp Gly Asn Arg Asn Arg Pro Ile Asn
1               5                   10

(2) INFORMATION FOR SEQ ID NO:18:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:18:

Pro Pro Arg Trp Gly Leu Asn Asn Arg Pro Ile Asn
1               5                   10

(2) INFORMATION FOR SEQ ID NO:19:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:19:

Pro Pro Arg Trp Gly Leu Arg Leu Arg Pro Ile Asn
1               5                   10

(2) INFORMATION FOR SEQ ID NO:20:

(i) SEQUENCE CHARACTERISTICS:
            (A) LENGTH: 12 amino acids
            (B) TYPE: amino acid

```
            (C) STRANDEDNESS: unknown
            (D) TOPOLOGY: unknown (ii) MOLECULE TYPE: protein (xi) SEQUENCE DESCRIPTION: SEQ ID NO:20:

Pro Pro Arg Trp Gly Leu Arg Asn Asn Pro Ile Asn
1               5                   10

(2) INFORMATION FOR SEQ ID NO:21:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:21:

Pro Pro Arg Trp Gly Leu Arg Asn Arg Pro Ile Asn
1               5                   10

(2) INFORMATION FOR SEQ ID NO:22:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:22:

Pro Arg Trp Gly Leu Arg Asn Arg Pro
1               5

(2) INFORMATION FOR SEQ ID NO:23:

(i) SEQUENCE CHARACTERISTICS:
            (A) LENGTH: 7 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:23:

Arg Trp Gly Leu Arg Asn Arg
1               5

(2) INFORMATION FOR SEQ ID NO:24:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO:24:

Pro Ala Arg Trp Gly Trp Arg His Gly Pro Ile Asn
1               5                   10

(2) INFORMATION FOR SEQ ID NO:25:

(i) SEQUENCE CHARACTERISTICS:
            (A) LENGTH: 9 amino acids
```

(B) TYPE: amino acid
           (C) STRANDEDNESS: unknown
           (D) TOPOLOGY: unknown (ii) MOLECULE TYPE: protein (xi) SEQUENCE DESCRIPTION: SEQ ID NO:25:

Ala Arg Trp Gly Trp Arg His Gly Pro
1               5

(2) INFORMATION FOR SEQ ID NO:26:

(i) SEQUENCE CHARACTERISTICS:
           (A) LENGTH: 6 amino acids
           (B) TYPE: amino acid
           (C) STRANDEDNESS: unknown
           (D) TOPOLOGY: unknown (ii) MOLECULE TYPE: protein (xi) SEQUENCE DESCRIPTION: SEQ ID NO:26:

Arg Trp Gly Trp Arg His
1               5

(2) INFORMATION FOR SEQ ID NO:27:

(i) SEQUENCE CHARACTERISTICS:
           (A) LENGTH: 5 amino acids
           (B) TYPE: amino acid
           (C) STRANDEDNESS: unknown
           (D) TOPOLOGY: unknown (ii) MOLECULE TYPE: protein (xi) SEQUENCE DESCRIPTION: SEQ ID NO:27:

Arg Trp Gly Trp Arg
1               5

(2) INFORMATION FOR SEQ ID NO:28:

(i) SEQUENCE CHARACTERISTICS:
           (A) LENGTH: 24 base pairs
           (B) TYPE: nucleic acid
           (C) STRANDEDNESS: unknown
           (D) TOPOLOGY: unknown (ii) MOLECULE TYPE: DNA (genomic)

(xi) SEQUENCE DESCRIPTION: SEQ ID NO:28:

AGGGCAGGCA GCATCCAGGG TCCT                                              24

(2) INFORMATION FOR SEQ ID NO:29:

(i) SEQUENCE CHARACTERISTICS:
           (A) LENGTH: 25 base pairs
           (B) TYPE: nucleic acid
           (C) STRANDEDNESS: unknown
           (D) TOPOLOGY: unknown (ii) MOLECULE TYPE: DNA (genomic)

(xi) SEQUENCE DESCRIPTION: SEQ ID NO:29:

TGTCCGGGTT GTTAAGGTCG TACTT                                             25

(2) INFORMATION FOR SEQ ID NO:30:

(i) SEQUENCE CHARACTERISTICS:
           (A) LENGTH: 25 base pairs
           (B) TYPE: nucleic acid

```
        (C) STRANDEDNESS: unknown
        (D) TOPOLOGY: unknown (ii) MOLECULE TYPE: DNA (genomic)

(xi) SEQUENCE DESCRIPTION: SEQ ID NO:30:

GAAGACCAAG ATGGTGGCTG CGTTG                                          25

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:31:

TTCAGGTTCA GCCGTGCAAT GACCA                                          25

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:32:

TCAGTCGCAT TTAGGATGAG TTTTG                                          25

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:33:

GGATGAGTTT TGTCGCCCAG AGAA                                           24

(2) INFORMATION FOR SEQ ID NO:34:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:34:

Arg Trp Gly Trp Arg His Gly
1               5
```

NINJURIN

This invention was made with government support under grant number CA 53524 awarded by the National Institutes of Health. The government has certain rights in the invention.

FIELD OF THE INVENTION

The invention relates to novel ninjurin proteins, nucleic acids and antibodies.

BACKGROUND OF THE INVENTION

A distinguishing characteristic of the peripheral nervous system (PNS), as opposed to the central nervous system (CNS), is its capacity for axonal regeneration after injury. The environment in which PNS axons regenerate consists of Schwann cells and their basal laminae, fibroblasts, collagen, degenerating myelin, and phagocytic cells (Fawcett, J. W. and Keynes, R. J. (1990). Annu. Rev. Neurosci. 13, 43–60; Bunge, R. and Griffin, J. W. (1992). The cell of Schwann. In Diseases of the Nervous system:Clinical Neurology. A. K. Asbury, G. M. McKhann, and W. I. McDonald, eds. (Philadelphia: WB Saunders), pp. 87–100). Among these components, Schwann cells are indispensable for axonal regeneration, as evidenced by the reduction in axonal growth when live Schwann cells are removed from the area of injury (Hall, S. M. (1986). Neuropathol. Appl. Neurobiol. 12, 401–414). Conversely, when transplants consisting of cultured Schwann cells and their associated extracellular matrix are introduced into a lesion in the CNS, axonal regeneration and subsequent re-innervation is facilitated, clearly indicating the unique role of Schwann cells in promoting axonal regeneration (Aguayo, A. J. (1985). Axonal regeneration from injured neurons in the adult mammalian central nervous system. In Synaptic plasticity and Remodeling. C. W. Cotman, ed. (New York: Guilford Press), pp. 457–483; Benfey et al., Nature 296, 150–152; Richardson et al., (1980). Nature 284, 264–265).

The interruption of the axon following nerve injury initiates a complex series of changes in the injured nerve. Rapid changes in the synthesis of myelin components occur, such as marked decreases in myelin lipid synthesis (Whiten et al., (1989) J. Neurochem. 52, 1085–1092) and diminished expression of the major myelin proteins (Trapp et al., (1988) J. Neurosci. 8, 3515–3521). Within three days after axotomy, Schwann cells in the distal stump begin to proliferate in a longitudinal band along which axonal regeneration and re-growth are most frequently observed (Chaudhry et al, (1992) Neurologic Clinics 10, 613–627). There are also a number of Schwann cell proteins whose expression is increased in the distal stump after nerve injury, including cell surface molecules like the p75 NGF receptor (Taniuchi et al., (1988) J. Neurosci. 8, 664–681), and cell adhesion molecules LI, N-cadherin and N-CAM, that are important for neurite outgrowth on Schwann cells in vitro (Martini et al., (1988) J. Cell. Biol. 106, 1746; Bixby et al., (1988) J. Cell. Biol. 107, 353–361; Rieger et al., (1988) J. Cell. Biol. 107, 707–719). Schwann cells also increase the expression of a number of diffusible molecules, including the neurotrophic factors, brain-derived neurotrophic factor (BDNF) and nerve growth factor (NGF), as well as apolipoprotein D, which may be involved in the recycling of cholesterol released from degenerating myelin (Spreyer et al, (1990) EMBO J 9, 2479–2484).

Most of the changes in Schwann cell phenotype in response to nerve injury appear to be dependent on the axon itself, as many of them are reversed as the axon regenerates. For instance, p75 expression is down-regulated in Schwann cells adjacent to the regenerating axon (Taniuchi et al., 1988) and in Schwann cells co-cultured with neurons (Tomaselli et al., (1986) J. Cell Biol. 103, 2659–2672; Fallon, J.R. (1985) J. Neurosci. 5, 3169–3177). In contrast, the expression of myelin proteins such as $P_0$ and PMP-22 increases as the axon regenerates and remyelination ensues (White et al., 1989; Snipes et al., (1992) J. Cell Biol. 117, 225–238). Most of the molecules that mediate alterations in Schwann cell gene expression remain obscure; one exception is the increased expression of NGF that is mediated by IL-1 elaborated by macrophages that invade the lesioned nerve (Lindholm et al., (1987) Nature 330, 658–659).

Cell surface adhesion proteins have also been shown to play a role in tissue regeneration after injury in a number of organisms. Cell surface adhesion proteins also play an important role in embryonic development and in the assembly of adult organs. In vertebrates, a number of cell surface glycoproteins have been identified as adhesion molecules, including integrins, cadherins, and those containing a immunoglobulin(Ig)-like motif.

The role of adhesion proteins in nerve regeneration has been documented (Martini, R. (1994) J. Neurocytology 23, 1–28; Brodkey et al., (1993) Exp. Neurol. 123, 251–270). The expression of a number of adhesion proteins is elevated after nerve injury, including N-CAM and L1, which are thought to be involved in forming a suitable substrate for the extension of the regenerating axons. The time course of this up-regulation has been reported (Daniloff et al., (1986) J. Cell Biol. 103, 929–945; Martini, 1994). Interestingly, the levels of N-CAM and L1 each return to normal more rapidly after a crush injury than after transection, in accord with the more rapid and complete recovery observed after nerve crush (Daniloff et al., 1986). Direct support for the role of adhesion proteins in promoting neurite outgrowth has come from the demonstration that neutralizing antibodies to L1 and N-cadherin inhibit Schwann cell stimulated neurite outgrowth from peripheral motor neurons (Seilheimer et al., J. Cell Biol. 107, 341–351). However, these studies also suggest that additional molecules are also important, as no single antibody or combination of antibodies was capable of totally eliminating process outgrowth. In the case of L1 and N-cadherin, homophilic interactions between molecules present on neuronal outgrowths and Schwann cells are likely to be responsible for their growth promoting effects (Lemmon et al., (1989) Neuron 2, 1597–1603; Takeichi, M. (1991) Science 251, 1451–1455).

The residues which mediate the adhesive interactions of these molecules have been identified for only a subset of these proteins. One of the most well-characterized sequence motifs of this type is the tripeptide Arg-Gly-Asp (RGD) which was identified as the sequence within fibronectin that mediates cell attachment. Many integrins recognize this RGD motif within their respective ligands, and these interactions then mediate either cell-substratum or cell-cell interactions.

Members of the cadherin family contain multiple copies of the sequences, Asp-Arg-Glu (DRE) and Asp-x-Asn-Asp-Asn (SEQ ID NO: 1) sequences. Structural analysis of cadherin indicates that these motifs may be situated such that they can form a zipper-like structure that may be critical for cell adhesion.

Shared sequence motifs for members of the Ig-superfamily of adhesion molecules have not been reported, although it has been proposed that a decapeptide sequence (KYSFNYDGSE) (SEQ ID NO: 2) in the third Ig-like domain of neural cell adhesion molecule (NCAM) is responsible for its homophilic binding interactions.

SUMMARY OF THE INVENTION

It is an object of the present invention to provide novel proteins which play a role in axonal regeneration of PNS neuronal cells after injury. Accordingly, the invention provides recombinant ninjurin proteins and variants thereof, and to produce useful quantities of these ninjurin proteins using recombinant DNA techniques.

It is a further object of the invention to provide recombinant nucleic acids encoding ninjurin proteins, and expression vectors and host cells containing the nucleic acid encoding the ninjurin protein.

An additional object of the invention is to provide polyclonal and monoclonal antibodies directed against ninjurin proteins.

A further object of the invention is to provide methods for producing the ninjurin proteins.

In accordance with the objects outlined above, the present invention provides recombinant nucleic acids encoding ninjurin proteins, including fragments of the full-length proteins, and ninjurin peptides. The ninjurin proteins include ninjurin 1 and ninjurin 2. The ninjurin peptides include variant or derivative ninjurin peptides.

In a further aspect, the invention provides expression vectors comprising transcriptional and translational regulatory DNA operably linked to DNA encoding a ninjurin protein, and host cells containing the expression vectors.

In an additional aspect, the invention provides methods for producing ninjurin proteins comprising the steps of culturing a host cell transformed with an expressing vector comprising a nucleic acid encoding a ninjurin protein and expressing the nucleic acid to produce a ninjurin protein.

In a further aspect, the invention provides recombinant ninjurin proteins including fragments of the full-length proteins, and ninjurin peptides, including derivative ninjurin peptides.

In an additional aspect, the invention provides pharmaceutical compositions comprising ninjurin proteins, and polypeptides capable of specifically binding to a ninjurin protein, including antibodies.

In a further aspect, the invention provides polyclonal or monoclonal antibodies to ninjurin proteins.

In an additional aspect, the invention provides METHODS OF TREATMENT, ETC.?

BRIEF DESCRIPTION OF THE DRAWINGS

FIGS. 1A and 1B depict the nucleotide sequence (FIG. 1A) (SEQ ID NO: 3) and amino acid sequence (FIG. 1B) (SEQ ID NO: 4) of rat ninjurin 1.

FIGS. 2A and 2B depict the nucleotide sequence (FIG. 2A) (SEQ ID NO: 5) and amino acid sequence (FIG. 2B) (SEQ ID NO: 6) of human ninjurin 1.

FIGS. 3A and 3B depict the nucleotide sequence (FIG. 3A) (SEQ ID NO: 7) and amino acid sequence (FIG. 3B) (SEQ ID NO: 8) of human ninjurin 2.

FIG. 4 depicts the nucleotide sequence (SEQ ID NO: 9) of variant 1 of human ninjurin 1.

FIG. 5 depicts the nucleotide sequence (SEQ ID NO: 10) of variant 1 of human ninjurin 2.

FIG. 6 depicts the nucleotide sequence (SEQ ID NO: 11) of variant 2 of human ninjurin 2.

FIG. 7 depicts the homology lineup of rat ninjurin 1 (SEQ ID NO: 4), human ninjurin 1 (SEQ ID NO: 6), and human ninjurin 2 (SEQ ID NO: 8).

FIGS. 8A, 8B and 8C show the peptides used to characterize the binding domain. FIG. 8A depicts the first 100 amino acids of the rat ninjurin 1 protein (SEQ ID NO: 13), with the overlapping peptides used to elucidate the binding domain. The double underlining shows the putative transmembrane domain. FIG. 8B depicts the 8 overlapping peptides used to localize the binding domain. The "+" or "−" next to the peptide shows the peptide's ability to inhibit the ninjurin-mediated aggregation. FIG. 8C shows the 7 peptides (SEQ ID NO: 14–20) used to identify the important binding residues. The single amino acid substitutions used to identify the important binding domain residues are shown in bold. Peptides 9 (SEQ ID NO: 14) (substitution of Arg28 (rat ninjurin 1 numbering) to Asn28), 10 (SEQ ID NO: 15) (substitution of Trp29 for Ala29), 13 (SEQ ID NO: 18) (substitution of Arg32 for Asn32), and 15 (SEQ ID NO: 20) (substitution of Arg34 for Asn34) were less active than peptide 6 for inhibition of adhesion, thus implicating these residues as functionally important for ninjurin adhesion. Peptides 11 (SEQ ID NO: 16) (substitution of Gly29 to Ala29), 12 (SEQ ID NO: 17) (substitution of Leu3 1 to Asn3 1) did not exhibit altered inhibition, thus suggesting these residues are not important in ninjurin binding. Peptide 14 (SEQ ID NO: 19) (substitution of Asn33 for Leu33) was actually more effective than the wild type peptide 6 in inhibiting ninjurin binding.

DETAILED DESCRIPTION OF THE INVENTION

The present invention provides novel ninjurin proteins. In a preferred embodiment, the ninjurin proteins are from vertebrates, more preferably from mammals, and in the preferred embodiment, from rats or humans. However, using the techniques outlined below, ninjurin proteins from other organisms may also be obtained.

As outlined herein, the ninjurin proteins of the present invention are cellular adhesion molecules which are expressed in a variety of tissue types. Ninjurin is a membrane bound protein, as it contains two putative transmembrane domains, with the extracellular domain containing at least one binding domain. The mechanism of adhesion includes (but is not limited to) a homophilic binding of ninjurin molecules on adjacent cells, i.e. the binding domain of ninjurin can self-aggregate. It is also possible that the mechanism of adhesion includes heterophilic interactions.

Without being bound by theory, it appears that there are a number of related ninjurin proteins and nucleic acids. For example, in the human, it appears that there are at least two separate ninjurin nucleic acids that encode two different ninjurin proteins, ninjurin 1 and ninjurin 2. In addition, the ninjurin nucleic acids also are alternatively spliced to produce further distinct ninjurin nucleic acids or variant ninjurin nucleic acids such as are depicted in FIGS. 4 (SEQ ID NO: 9), 5 (SEQ ID NO: 10) and 6 (SEQ ID NO: 11). All of these ninjurins share basic homology to each other, and a marked lack of homology to any other known proteins or nucleic acids.

Thus, a ninjurin protein of the present invention may be identified in several ways. A ninjurin nucleic acid or ninjurin protein is initially identified by substantial nucleic acid and/or amino acid sequence homology to the sequences shown in FIGS. 1 (SEQ ID NOS: 3 and 4), 2 (SEQ ID NOS: 5 and 6), 3 (SEQ ID NOS: 7 and 8), 4 (SEQ ID NO: 9), 5

(SEQ ID NO: 10) or 6 (SEQ ID NO: 11). Such homology can be based upon the overall nucleic acid or amino acid sequence.

As used herein, a protein is a "ninjurin protein" if the overall homology of the protein sequence to the amino acid sequences shown in FIGS. 1 (SEQ ID NOS: 3 and 4), 2 (SEQ ID NOS: 5 and 6) or 3 (SEQ ID NOS: 7 and 8) is preferably greater than about 40%, more preferably greater than about 50% and most preferably greater than 75%. In some embodiments the homology will be as high as about 90 to 95 or 98%. This homology will be determined using standard techniques known in the art, such as the Best Fit sequence program described by Devereux et al., NucL. Acid Res. 12:387–395 (1984) or the BLASTX program (Altschul et al., J. Mol. Biol. 215, 403–410). The alignment may include the introduction of gaps in the sequences to be aligned. In addition, for sequences which contain either more or fewer amino acids than the proteins shown in the Figures, it is understood that the percentage of homology will be determined based on the number of homologous amino acids in relation to the total number of amino acids. Thus, for example, homology of sequences shorter than that shown in the Figures, as discussed below, will be determined using the number of amino acids in the shorter sequence.

As discussed above, ninjurin proteins include ninjurin 1 and ninjurin 2 proteins. Ninjurin proteins may be identified in one aspect by significant homology to at least one and preferably both of the transmembrane domains, as these domains are quite unique. Thus, a ninjurin 1 protein is characterized by homology to the rat and human ninjurin 1 proteins depicted in FIGS. 1B (SEQ ID NO: 4) and 2B (SEQ ID NO: 6). This homology is preferably greater than about 50%, with greater than about 70% being particularly preferred and greater than about 85% being especially preferred. In some cases the homology will be greater than about 90 to 95 or 98%. As discussed herein, the rat and human ninjurin 1 proteins are roughly 90% homologous to each other. Preferably, a ninjurin 1 protein also has significant homology to the ninjurin 1 binding domain as described herein. Similarly, a ninjurin 2 protein is characterized by homology to the human ninjurin 2 protein. This homology is preferably greater than about 50%, with greater than about 70% being particularly preferred and greater than about 85% being especially preferred. In some cases the homology will be greater than about 90 to 95 or 98%. Ninjurin 1 and 2 proteins are homologous to each other, with the ninjurin 1 and 2 proteins from human being roughly 55% homologous to each other.

Ninjurin proteins of the present invention may be shorter or longer than the amino acid sequences shown in the Figures. Thus, in a preferred embodiment, included within the definition of ninjurin proteins are portions or fragments of the sequences shown in FIGS. 1 (SEQ ID NOS: 3 and 4), 2 (SEQ ID NOS: 5 and 6) and 3 (SEQ ID NOS: 7 and 8). As outlined in the Examples, ninjurin peptides can be made which comprise the ninjurin 1 binding domain of rat ninjurin and human ninjurin 1. These ninjurin peptides will bind to the binding domain of the full length protein, or to each other, thus preventing or decreasing their ability to bind other binding domains, and thus interfering with cellular adhesion. Alternatively, longer fragments of ninjurin proteins can be made, or fragments of ninjurin which do not contain the binding domain. A preferred ninjurin fragment is the extracellular domain of ninjurin, comprising roughly the first 70 amino acids of ninjurin I or the about the first 55 amino acids of ninjurin 2.

Furthermore, as outlined in the Examples, there are at least two distinct human ninjurin genes, encoding two ninjurin proteins. In addition, the mRNA for these two genes can be alternatively spliced. These alternatively spliced forms are also included with the definition of a ninjurin nucleic acid, despite the lack of significant amino acid sequence and a ninjurin 1 binding domain in the putative coding region.

Thus, in a preferred embodiment, the ninjurin proteins of the present invention are ninjurin peptides. In this embodiment, a ninjurin peptide comprises at least the ninjurin 1 binding domain, although it may contain additional amino acids as well. As shown in the Examples and discussed below, ninjurin is a homophilic adhesion protein. A "binding domain", i.e. a portion of the protein that associates during cellular aggregation, will bind to other ninjurin binding domains. The ninjurin 1 binding domain for the rat and human ninjurin 1 protein has been identified as shown in the Examples. The ninjurin 1 binding domain includes the amino acid residues corresponding to residues 26–37 of the rat or human ninjurin 1, with at least residues corresponding to amino acids numbers 28–35 preferably being present. The rat and human ninjurin 1 sequences are 70% homologous as between residues 26–37, and 57% homologous as between residues 2–35. Thus, in a preferred embodiment, a ninjurin protein or peptide may be identified by the presence of a binding domain. A ninjurin 1 protein or peptide contains a ninjurin 1 binding domain.

A ninjurin 2 protein or peptide may contain a ninjurin 2 binding domain. In a preferred embodiment, the binding domain is at least about 50% homologous to any of the binding domains depicted in FIG. 7 (SEQ ID NO: 4,6,8 and 12), with at least about 60% being preferred, and at least about 70% being particularly preferred. In some embodiments the homology will be as high as about 85% or 90%, with 95% and 98% being particularly preferred.

Thus, a ninjurin peptide is a short protein that contains a homologous binding domain as outlined above. The ninjurin peptides are preferably at least about 7 or 10 to 15 amino acids long, although longer peptides which include all or part of the binding domain may also be used, as well as other amino acid residues if desirable. It should be appreciated that the exact length of the ninjurin peptide may vary. Preferred embodiments of ninjurin 1 peptides include, but are not limited to, (from rat ninjurin 1) Pro-Pro-Arg-Trp-Gly-Leu-Arg-Asn-Arg-Pro-Ile-Asn (SEQ ID NO: 21), Pro-Arg-Trp-Gly-Leu-Arg-Asn-Arg-Pro (SEQ ID NO: 22), and Arg-Trp-Gly-Leu-Arg-Asn-Arg (SEQ ID NO: 23). Preferred ninjurin 1 peptides from human ninjurin 1 include, but are not limited to, Pro-Ala-Arg-Trp-Gly-Trp-Arg-His-Gly-Pro-Ile-Asn (SEQ ID NO: 24), Ala-Arg-Trp-Gly-Trp-Arg-His-Gly-Pro (SEQ ID NO: 25), Arg-Trp-Gly-Trp-Arg-His (SEQ ID NO: 26), and Arg-Trp-Gly-Trp-Arg (SEQ ID NO: 27).

However, not all ninjurin proteins contain a complete ninjurin 1 binding domain. For example, hunan ninjurin 2 does not appear to contain a complete ninjuurin 1 binding domain. In addition, it appears that there are variant forms of the ninjurin genes that do not contain ninjurin 1 binding domains. Ninjurin 2 proteins may contain an as yet unidentified ninjurin 2 binding domain. The ninjurin 2 binding domain may be easily identified by those skilled in the art as is outlined in the Examples for ninjurin 1. For example, overlapping peptides of ninjurin 2 are made and tested in ninjurin mediated binding assays. Peptides which inhibit ninjurin mediated binding contain all or portion of a ninjurin 2 binding domain. The ninjurin 2 binding domain may be further identified using site directed mutagenesis as outlined in Example 2.

In a preferred embodiment, the ninjurin peptides are derivative or variant ninjurin peptides, either of ninjurin 1 or 2 or others. That is, the derivative ninjurin peptide will contain at least one amino acid substitution, deletion or insertion, with amino acid substitutions being particularly preferred. The amino acid substitution, insertion or deletion may occur at any residue within the ninjurin peptide. As outlined below, particularly preferred substitutions are made at positions corresponding to rat ninjurin 1 at position 28, 29, 31, 32, 33 and 34. The derivative ninjurin peptide can be less effective or more effective in binding to another binding domain of either another ninjurin peptide or a full length ninjurin protein, or may not alter the binding characteristics. By "less effective" herein is meant that the mutation comprising the derivative peptide makes the peptide less active for inhibition of ninjurin mediated adhesion than the wild-type ninjurin peptide. By "more effective" herein is meant that the derivative peptide is more active for inhibition of ninjurin mediated adhesion than the wild-type ninjurin peptide, i.e. the derivative binds the binding domain more tightly.

Ninjurin proteins may also be identified as being encoded by ninjurin nucleic acids. Thus, ninjurin proteins are encoded by nucleic acids that will hybridize to the sequences depicted in FIGS. 1–6 (SEQ ID NO: 3–11), as outlined herein.

In a preferred embodiment, when the ninjurin protein is to be used to generate antibodies, the ninjurin protein must share at least one epitope or determinant with the full length proteins shown in FIGS. 1 (SEQ ID NOS: 3 and 4), 2 (SEQ ID NOS: 5 and 6), 3 (SEQ ID NOS: 7 and 8), 4 (SEQ ID NO: 9), 5 (SEQ ID NO: 10), and 6 (SEQ ID NO: 11). By "epitope" or "determinant" herein is meant a portion of a protein which will generate and/or bind an antibody. Thus, in most instances, antibodies made to a smaller ninjurin protein will be able to bind to the full length protein. In a preferred embodiment, the epitope is unique; that is, antibodies generated to a unique epitope show little or no cross-reactivity. In a preferred embodiment, the antibodies are generated to a ninjurin binding domain. In some instances, the antibody may recognize both ninjurin 1 and 2 molecules; alternatively, antibodies may be generated that do not cross-react as between ninjurin 1 and ninjurin 2. In a preferred embodiment, the antibodies are generated to an extracellular portion of the ninjurin molecule, i.e. to all or some of the N-terminal region from amino acid numbers 1–71. The ninjurin antibodies of the invention specifically bind to ninjurin proteins. By "specifically bind" herein is meant that the antibodies bind to the protein with a binding constant in the range of at least $10^4$–$10^6$ $M^{-1}$, with a preferred range being $10^7$–$10^9$ $M^{-1}$.

In the case of the nucleic acid, the overall homology of the nucleic acid sequence is commensurate with amino acid homology but takes into account the degeneracy in the genetic code and codon bias of different organisms.

Accordingly, the nucleic acid sequence homology may be either lower or higher than that of the protein sequence. Thus the homology of the nucleic acid sequence as compared to the nucleic acid sequences of FIGS. 1 (SEQ ID NOS: 3 and 4), 2 (SEQ ID NOS: 5 and 6), 3 (SEQ ID NOS: 7 and 8), 4 (SEQ ID NO. 9), 5 (SEQ ID NO: 10) or 6 (SEQ ID NO: 11) is preferably greater than 40%, more preferably greater than about 45%, particularly greater than about 50% and most preferably greater than 55%. In some embodiments the homology will be as high as about 70, 80, 90 to 95 or 98%. The homology of the nucleic acid sequence of rat ninjurin 1 and human ninjurin 1 is 73%; as between rat ninjurin 1 and human ninjurin 2 the homology is 52%; and as between human ninjurin 1 and 2 the homology is 55%.

In a preferred embodiment, a ninjurin nucleic acid encodes a ninjurin protein; ninjurin 1 nucleic acids encode ninjurin 1 proteins, and ninjurin 2 nucleic acids encode ninjurin 2 proteins. As will be appreciated by those in the art, due to the degeneracy of the genetic code, an extremely large number of nucleic acids may be made, all of which encode the ninjurin proteins of the present invention. Thus, having identified a particular amino acid sequence, those skilled in the art could make any number of different nucleic acids, by simply modifying the sequence of one or more codons in a way which does not change the amino acid sequence of the ninjurin.

In one embodiment, the nucleic acid homology is determined through hybridization studies. Thus, for example, nucleic acids which hybridize under high stringency to the nucleic acid sequences shown in FIGS. 1–6 or their complements are considered ninjurin genes. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference.

In another embodiment, less stringent hybridization conditions are used; for example, moderate or low stringency conditions may be used, as are known in the art; see Maniatis and Ausubel, supra.

The ninjurin proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. By the term "recombinant nucleic acid" herein is meant nucleic acid, originally formed in vitro, in general, by the manipulation of nucleic acid by endonucleases, in a form not normally found in nature. Thus an isolated ninjurin nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a ninjurin protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Also included with the definition of ninjurin protein are other ninjurin proteins of the ninjurin family, and ninjurin proteins from other organisms, which are cloned and expressed as outlined below. Thus, probe or degenerate polymerase chain reaction (PCR) primer sequences may be used to find other related ninjurin proteins from humans or other organisms. As will be appreciated by those in the art, particularly useful probe and/or PCR primer sequences include the unique areas of the ninjurin nucleic acid sequence. Thus, useful probe or primer sequences may be designed to: a) all or part of the sequence of the unique ninjurin 1 binding domain; b) all or part of the unique first putative transmembrane domain, which spans roughly amino acids 72 to 100 in rat and human ninjurin 1 and amino acids 59 to 87 in human ninjurin 2, with residues 70–80 (ninjurin 1) and 57–67 (ninjurin 2) being particularly useful due to the presence of phenylalanine and tryptophan; c) all or part of the unique second putative transmembrane domain, which spans roughly amino acids 118–139 in rat and human ninjurin 1 and amino acids 105–126 in human ninjurin 2; and d) all or part of the residues from about 50 to about 70 in ninjurin 1 and 37–77 of ninjurin 2, due to the presence of conserved methionines. As is generally known in the art, preferred PCR primers are from about 15 to about 35 nucleotides in length, with from about 20 to about 30 being preferred, and may contain inosine as needed. The conditions for the PCR reaction are well known in the art.

Once the ninjurin nucleic acid is identified, it can be cloned and, if necessary, its constituent parts recombined to form the entire ninjurin protein nucleic acid. Once isolated from its natural source, e.g., contained within a plasmid or other vector or excised therefrom as a linear nucleic acid segment, the recombinant ninjurin nucleic acid can be further used as a probe to identify and isolate other ninjurin nucleic acids. It can also be used as a "precursor" nucleic acid to make modified or variant ninjurin nucleic acids and proteins.

Using the nucleic acids of the present invention which encode a ninjurin protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the ninjurin protein. "Operably linked" in this context means that the transcriptional and translational regulatory DNA is positioned relative to the coding sequence of the ninjurin protein in such a manner that transcription is initiated. Generally, this will mean that the promoter and transcriptional initiation or start sequences are positioned 5' to the ninjurin protein coding region. The transcriptional and translational regulatory nucleic acid will generally be appropriate to the host cell used to express the ninjurin protein; for example, transcriptional and translational regulatory nucleic acid sequences from Bacillus are preferably used to express the ninjurin protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The ninjurin proteins of the present invention are produced by culturing a host cell transformed with an expression vector containing nucleic acid encoding a ninjurin protein, under the appropriate conditions to induce or cause expression of the ninjurin protein. The conditions appropriate for ninjurin protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, and HeLa cells, fibroblasts, Schwanoma cell lines, and immortalized mammalian myeloid, lymphoid cell lines.

In a preferred embodiment, the ninjurin proteins are expressed in mammalian cells. Mammalian expression systems are also known in the art. A mammalian promoter is any DNA sequence capable of binding mammalian RNA polymerase and initiating the downstream (3') transcription of a coding sequence for ninjurin protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide (s) in liposomes, and direct microinjection of the DNA into nuclei.

In a preferred embodiment, ninjurin proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of ninjurin protein into MRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgamo (SD) sequence and includes an initiation codon and a sequence 3–9 nucleotides in length located 3–11 nucleotides upstream of the initiation codon.

The expression vector may also include a signal peptide sequence that provides for secretion of the ninjurin protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, ninjurin proteins are produced in insect cells. Expression vectors for the transformation of insect cells, and in particular, baculovirus-based expression vectors, are well known in the art.

In a preferred embodiment, ninjurin protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUPI gene, which allows yeast to grow in the presence of copper ions.

The ninjurin protein may also be made as a fusion protein, using techniques well known in the art. Thus, for example, for the creation of monoclonal antibodies, if the desired epitope is small, the ninjurin protein may be fused to a carrier protein to form an immunogen. Alternatively, the ninjurin protein may be made as a fusion protein to increase expression, or for other reasons. For example, when the ninjurin protein is a ninjurin peptide, the nucleic acid encoding the peptide may be linked to other nucleic acid for expression purposes.

Also included within the definition of ninjurin proteins of the present invention are amino acid sequence variants. These variants fall into one or more of three classes: substitutional, insertional or deletional variants. These variants ordinarily are prepared by site specific mutagenesis of nucleotides in the DNA encoding the ninjurin protein, using cassette or PCR mutagenesis or other techniques well known in the art, to produce DNA encoding the variant, and thereafter expressing the DNA in recombinant cell culture as outlined above. However, variant ninjurin protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the ninjurin protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed ninjurin variants screened for the optimal combination of desired activity. Techniques for making substitution mutations at predetermined sites in DNA having a known sequence are well known, for example, M13 primer mutagenesis and PCR mutagenesis. Screening of the mutants is done using assays of ninjurin protein activities; for example, for binding domain mutations, competitive binding studies such as are outlined in the Examples may be done.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger. For example, a preferred deletion variant is the deletion of the transmembrane domains and the cytoplasmic domain, leaving only the extracellular domain of ninjurin, i.e. a soluble receptor. The extracellular domain of ninjurin 1 comprises the N-terminal 70 or so amino acids, and the extracellular domain of ninjurin 2 comprises the N-terminal 57 or so amino acids.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the ninjurin protein are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the ninjurin proteins as needed. Alternatively, the variant may be designed such that the biological activity of the ninjurin protein is altered. For example, the N-glycosylation site may be altered or removed. Either or both of the transmembrane domains may be altered or removed, to make a soluble or secreted protein, i.e. the extracellular domain.

In a preferred embodiment, binding domain variants are made. In one embodiment, a binding domain may be eliminated entirely. Alternatively, any or all of the amino acids of a binding domain may be be altered or deleted. In a preferred embodiment, one or more of the amino acids of the binding domain are substituted by other amino acids. Thus, amino acids corresponding to the rat ninjurin 1 binding domain residues may be altered, including, but not limited to, residues corresponding to Pro26, Pro27, Arg28, Trp29, Gly30, Leu31, Arg32, Asn33, Arg34, Pro35, Ile36 or Asn37. Particularly preferred are alterations at Arg28, Trp29, Arg32, Asn33 and Arg34, alone or in combination. Any amino acid may be substituted. In particular, modifications at position 33 can increase the binding affinity of the molecule. Similarly, the amino acids of the human ninjurin 1 binding domain may be altered, including, but not limited to, residues corresponding to Pro26, Ala27, Arg28, Trp29, Gly30, Trp31, Arg32, His33, Gly34, Pro35, Ile36, or Asn37, alone or in combination, with alterations at Arg28, Trp29, Trp31, Arg32 and His33 being particularly preferred. Again, any amino acid may be substituted. Similarly, the residues within the putative ninjurin 1 binding domain of human ninjurin 2 may be altered, including residues corresponding to Arg32, Ser33, Gln34, Pro35, Ile36 and Asn37 (rat ninjurin 1 numbering). Furthermore, human ninjurin 2 protein may be altered to contain a complete ninjurin 1 binding domain.

In addition, as outlined in the Examples, the homophilic ninjurin 1 cellular adhesion is dependent on the presence of divalent cations; thus, the metal binding properties of the binding domain may be altered.

In one embodiment, the ninjurin nucleic acids, proteins and antibodies of the invention are labelled. By "labelled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the ninjurin protein is purified or isolated after expression. Ninjurin proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the ninjurin protein may be purified using a standard anti-ninjurin antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the ninjurin protein. In some instances no purification will be necessary.

Once expressed and purified if necessary, the ninjurin proteins are useful in a number of applications.

In a preferred embodiment, the ninjurin proteins, and particularly ninjurin peptides, are useful in the study or treatment or other conditions which are mediated by ninjurin, i.e. to treat or prevent ninjurin-mediated disorders. Thus, "ninjurin mediated disorders" include conditions involving inappropriate (i.e. excessive or insufficient) cellular adhesion. Undesirable (i.e. excessive) cellular adhesion has been implicated in a large number of conditions, including, but not limited to, inflammatory diseases such as rheumatoid arthritis, asthma, allergy conditions, adult respiratory distress syndrome, inflammatory bowel diseases (e.g. Crohn's disease, ulcerative colitis and regional enteritis) and opthalmic inflammatory diseases; autoimmune diseases; thrombosis or inappropriate platelet aggregation conditions; arteriosclerosis; reocculusion following thrombolysis; cardiovascular diseases; some forms of diabetes and neoplastic disease including metastasis conditions. See generally WO 93/08823 and WO 95/17412, hereby incorporated by reference, which discuss the role of other cellular adhesion molecules in a number of diseases, which may also be mediated by ninjurin.

Thus, in a preferred embodiment, ninjurin proteins or peptides comprising the binding domain are made as "blocking peptides" for the treatment of undesirable cellular adhesion. These peptides can be used as competitive binding proteins for ninjurin mediated adhesion, thus effectively decreasing or blocking adhesion. Thus, any physiological process that depends on ninjurin mediated adhesion for biological finction may be altered by the use of ninjurin blocking peptides or ninjurin proteins. For example, adhesion events in inflammatory responses are known, including cell migration of macrophages to the site of inflammation, which may be blocked by the addition of competing binding domains, either as peptides, larger fragments or the full length proteins. Similarly, cell adhesion also contributes to metastasis of cancerous tumors, and blocking peptides could be used which would prevent cellular adhesion of metastasizing tumor cells. Furthermore, conditions which have active vascularization, such as in rapidly growing tumor cells, and diabetic retinopathy may rely on ninjurin mediated adhesion for neovascularization, and may be treated or altered via the use of blocking peptides. Additionally, harmful blood clotting may also be caused by inappropriate cell adhesion, particularly cell adhesion to the extracellular matrix, such as in arteriosclerosis, which could be prevented by the administration of a ninjurin peptide or protein that would function as an antagonist. Thus, proteins or polypeptides that specifically bind to ninjurin proteins may be made and used, which may be ninjurin proteins, including fragments of ninjurin proteins and ninjurin peptides, as well as ninjurin antibodies, discussed below.

Alternatively, cellular adhesion may also be desirable in some applications. Thus, for example, in a preferred embodiment, ninjurin proteins or peptides are used to promote nerve regeneration. For example, ninjurin nucleic acids may be used to transform cells which then express ninjurin at a high density at the surface. The cells may then be transplanted into a site of nerve damage to promote nerve regeneration. Similarly, ninjurin proteins or peptides may be made and incorporated into a matrix such as a gel matrix to promote nerve regeneration. Additionally, wound healing may be prolonged when cellular adhesion is insufficient; a ninjurin protein or peptide may be attached to a surface, matrix or cell and used to promote wound healing. Similarly, in prosthetic implantation, coating the prosthesis with ninjurin proteins would promote cellular adhesion and minimize rejection.

In one embodiment, the ninjurin proteins of the present invention may be used to generate polyclonal and monoclonal antibodies to ninjurin proteins, which are useful as described below. Similarly, the ninjurin proteins can be coupled, using standard technology, to affinity chromatography columns. These columns may then be used to purify ninjurin antibodies. In a preferred embodiment, the antibodies are generated to epitopes unique to the ninjurin protein; that is, the antibodies show little or no cross-reactivity to other proteins. These antibodies find use in a number of applications. For example, the ninjurin antibodies may be coupled to standard affinity chromatography columns and used to purify ninjurin proteins. The antibodies may also be used as blocking polypeptides, as outlined above, since they will specifically bind to the ninjurin protein.

The polypeptides that specifically bind to ninjurin, i.e. ninjurin proteins and ninjurin antibodies, may be used in the diagnosis of ninjurin-mediated disorders. Thus, the presence or absence or ninjurin may be assayed or detected using labelled ninjurin proteins, antibodies or nucleic acids. For example, methods are provided for detecting a ninjurin protein in a target sample comprising contacting a labelled polypeptide which will specifically bind to a ninjurin protein with the target sample and assaying for the presence of binding between the labelled polypeptide and ninjurin, if present, in the target sample. The contacting is done under conditions which allow binding to ninjurin. Thus, lymphocytes may be screened for the presence or absence of ninjurin.

The ninjurin proteins herein also find use as a target in screening assays for the development of ninjurin antagonists.

In the preferred embodiment, the ninjurin proteins of the present invention are administered to a patient to mediate ninjurin related adhesion, as outlined above.

In this embodiment, a therapeutically effective dose of a ninjurin is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for ninjurin degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the ninjurin proteins of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the ninjurin may be directly applied as a solution or spray.

The pharmaceutical compositions of the present invention comprise a ninjurin in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Cloning and characterization of rat ninjurin

Animals and surgical procedures. All surgical procedures followed the NIH guidelines for care and use of laboratory animals at Washington University. Male Sprague-Dawley rats (200–300 g) were anesthetized, and the right sciatic nerve was injured at the hip level either by transection or by compressing the nerve with forceps for 30 sec (crush). The contralateral nerve was exposed, but left uninjured (control). After the indicated length of time, the animals were euthanized and either perfused with 4% paraformaldehyde/phosphate buffered saline (PBS) for immunohistochemical analysis or decapitated for immediate collection of tissues for RNA isolation or in situ hybridization analysis. For nerve ligation experiments, the nerve was tightly ligated at the level of the hip using a 4–0 nylon suture. When indicated, the nerve was transected 5–8 mm distal to the ligation site. For analysis of E17 and E19 embryos, timed pregnant rats of the indicated gestational age were sacrificed and the embryos were immediately frozen. All tissue samples were stored at −70 C.

Construction and Screening of Sciatic Nerve cDNA libraries. To identify genes regulated in Schwann cells by nerve injury, two rat sciatic nerve cDNA libraries (normal vs. injured) were constructed in the λZAPII vector (Stratagene). The first was made using poly[$A^+$]RNA isolated from normal sciatic nerve, whereas the other was made using equivalent amounts of poly[$A^+$]RNA isolated from 16 hr, 3 d and 7 d post-axotomy nerve segments (both proximal neuroma and distal segment). The RNA templates were used to synthesize cDNA as previously described (Gubler et al., (1983) Gene 25, 263–269). The cDNAs were cloned into EcoR1/Not1 digested λZAPII phage arms, the phage were packaged in vitro (Gigapack Gold; Stratagene) and used to infect E. coli XL-1 Blue strain (Stratagene). To enrich for cDNA clones whose mRNAs are upregulated in response to axotomy, a subtracted injured nerve library was obtained using a minor modification of a previously described method (Rubenstein et al., (1990) Nucleic Acids Res 18, 4833–4842). RNA was transcribed from the normal nerve cDNA library and biotinylated using Photobiotin (Vector Laboratories, CA). This biotinylated RNA was hybridized to single-stranded phagemid prepared from the injured nerve library and heteroduplexes and unhybridized driver RNA was removed with streptavidin Sepharose beads (Sigma). The remaining single-stranded phagemid was converted to double-stranded form with Taq polymerase and transformed into XL-1 Blue bacteria. This subtracted library was differentially screened by hybridizing with $^{32}$P-labeled first strand cDNAs prepared by reverse transcription of poly[$A^+$]RNA extracted from either distal portion of the transected sciatic nerve (7 days after transection) or sciatic nerves of the contralateral side (control) as previously described (Maniatis et al.,(1982). Molecular cloning: A laboratory manual. Cold Spring Harbor Laboratory 1, 280–281). Plaques that gave a signal of differential intensity between the two probes were re-plated and re-screened with the same probes, and clones corresponding to mRNAs which are differentially regulated in normal vs. injured nerve were identified. This screen resulted in the identification of a 1113 nt cDNA clone which corresponded to an mRNA that was induced in response to nerve injury.

To obtain additional ninjurin cDNA clones, the injured nerve cDNA library was screened with the $^{32}$P-labeled fragment from the initial cDNA clone. Three independent ninjurin clones were isolated. The 5'-terminal end of the ninjurin cDNA was obtained using the RACE (rapid amplification of cDNA end) technique using the 5'-AmplifinderRACE kit (Clontech) with RNA prepared from distal sciatic nerve 3 d post-axotomy and oligonucleotides corresponding to nt 117–143 and 177–201 of the ninjurin cDNA sequence. The nucleotide sequence of multiple ninjurin cDNA clones was determined for both strands using a Model 373 automated sequencer (Applied Biosystems Inc, Foster City, Calif.).

The nucleotide sequences of these clones and of 5' end RACE amplification products revealed a cDNA that was 1142 nt in length, in good correspondence with the 1.1 kb size estimated for the ninjurin mRNA. The sequence of this cDNA, which we have named ninjurin, for Nerve Injury Induced protein contains an open reading frame of 152 amino acids that predicts a 16.3 kD protein. The nucleotide sequence surrounding the predicted initiator methionine conforms to the Kozak consensus for efficient translation. The 3'-noncoding sequence contains a polyadenylation signal sequence (AATAAA) 22 nucleotides away from the 3'-terminal poly(A) tail.

The ninjurin sequence was used to search the non-redundant nucleotide and amino acid sequence databases, but no homology to other proteins was detected. Analysis of potential structural motifs of ninjurin using computer programs that predict hydrophobicity (Kyte, et al., (1982) J. Mol. Biol. 157, 105–132), protein localization sites (Nakai et al., (1992)Genomics 25, 897–911), and protein secondary structure (Rost et al., (1995) Protein Science 4, 521–533), predict two possible transmembrane domains (residues 72–100, and 118–139). The amino terminal region of ninjurin, which is predicted to be outside of the cell from this analysis, is generally hydrophilic and contains one putative N-glycosylation site. No signal sequence is present, nor are there other sequence motifs indicative of a specific function or intracellular location.

Analysis of RNA expression patterns. Total RNA was prepared from tissues and samples (10 μg) were electrophoresed on 1% agarose/formaldehyde gels and blotted onto nylon membranes as previously described (Chomczynski et al., (1987) Anal. Biochem. 162, 156–159). Membranes were probed with a $^{32}$p labeled fragment of the ninjurin cDNA. In situ hybridization histochemistry was performed using $^{32}$P-labeled antisense or sense RNA probes transcribed from the ninjurin cDNA (nt 518–1026) on fresh frozen tissue samples as previously described (Wanaka et al., (1990) Neuron 5, 267–281).

To investigate the expression pattern of ninjurin after sciatic nerve axotomy, RNA was isolated from the distal segments of the transected nerve as well as the intact, contralateral nerve (control) at selected times after surgery. Ninjurin mRNA levels were very low in uninjured sciatic nerve, but were dramatically upregulated in the segment distal to the injury (either transection or crush) (data not shown) Ninjurin mRNA was detected within 3 hr after injury, and reached peak levels 7–14 days after the injury. Ninjurin mRNA levels remained elevated for up to 56 days post-transection, whereas after crush injury, which permits axonal regeneration, ninjurin expression returned to a low level by day 28. This time course correlates well with the nerve regeneration process, in which axonal regeneration is generally completed within several months after a crush injury, but is delayed or prevented after transection (Daniloff et al., 1986). These changes in ninjurin expression after nerve injury were confirmed by in situ hybridization analysis on nerves (transected vs. intact contralateral) harvested 7 days after axotomy. Ninjurin mRNA was detected throughout the distal segment and at the end of the proximal segment (i.e. proximal neuroma), whereas no signal was observed in the normal sciatic nerve (Data not shown). No difference in intensity was observed throughout the length of the distal segment.

To examine the tissue distribution of ninjurin, RNA blot analysis on samples isolated from a variety of adult rat tissues were performed. The highest levels of ninjurin mRNA were found in the liver. In addition, thymus, heart, adrenal gland and spleen also had significant levels of ninjurin transcripts, whereas brain and dorsal root ganglia (DRG) had low levels of expression (Data not shown). To examine ninjurin expression during development, in situ hybridization was performed on rat embryos sacrificed at embryonic days 17 and 19. Ninjurin expression is observed in a variety of embryonic tissues, with the most abundant expression observed in tissues where it is highly expressed in the adult (e.g. liver, adrenals, and spleen) (FIG. 3). Tissues hybridized with a ninjurin sense probe or tissues treated with ribonuclease prior to hybridization did not give any signal (data not shown). Ninjurin was also detected in the vertebra and limbs, where its expression increased with increasing embryonic age. The signal was detected primarily in regions of active ossification, such as the terminal areas of the limb and vertebral bones. The most intense signal was observed over layers of dividing chondrocytes, rather than over regions which were already ossified. Ninjurin was also highly expressed in the skin, and was primarily detected in the epithelium. In the central nervous system, ninjurin expression was very low throughout the embryonic period examined.

Generation and analysis of antibodies to ninjurin. A synthetic peptide containing an N-terminal cysteine and ninjurin residues 1 through 15 was conjugated to keyhole limpet hemocyanine using either glutaraldehyde or m-maleimidobenzoyl-n-hydroxysuccinimide ester. The conjugate proteins were used to immunize rabbits following standard procedures (Cocalico, PA) and anti-ninjurin antibodies were purified by chromatography over an affinity column in which the peptide was linked to SulfoLink Gel (Pierce) per manufacturer's instructions. Protein blot analysis was performed as previously described (Lee et al., (1995) Journal of Biological Chemistry 270, 9971–9977). Immunohistochemical analysis of rat tissues was performed on 15 micron sections of 4% paraformaldehyde fixed tissues using standard methods. The purified anti-ninjurin antiserum was used at a 1:2500 dilution and specific staining was detected with indocarbocyanine (Cy3)-conjugated anti-rabbit IgG (Jackson Lab). Glial fibrillary acidic protein (GFAP) was detected using an anti-GFAP monoclonal antibody (BRL) and fluorescein-conjugated anti-mouse IgG.

These antibodies recognized a 22 kD protein that was present in rat liver and in Chinese hamster ovary (CHO) cells stably transfected with a ninjurin expression vector, but not in native CHO cells (Data not shown). The size of the detected protein (22 kD) was larger than predicted from the cDNA sequence. Ninjurin was then tested to see if it was modified post-translationally. Ninjurin was immunoprecipitated with anti-ninjurin antibodies from lysates of the ninjurin-expressing CHO cells, and treated with either peptide:N-glycosidase F to remove any N-linked carbohydrates, or with alkaline phosphatase to remove any phosphate groups. After treatment, the proteins were electrophoresed on SDS-polyacrylamide gels. No differences in mobility were observed, suggesting that ninjurin is not modified in either of these manners (data not shown). Furthermore, the mobility of in vitro translated ninjurin also migrates slower than would be expected from its predicted size.

To further define the ninjurin expression pattern after nerve injury, an immunohistochemical analysis was performed using these anti-ninjurin antibodies. These studies clearly confirmed the upregulation of ninjurin after sciatic nerve injury. Ninjurin immunoreactive cells were detected within the proximal neuroma, and in the nerve segment distal to the site of transection (Data not shown). The ninjurin-positive cells were arranged in a parallel linear array, characteristic of the Schwann cells and their basal lamina (bands of Bungner) that are formed after degeneration of the axons and prior to their re-growth. Proximal to the transection site, Schwann cells did not contain significant amounts of ninjurin, except in the neuroma formed at the transection site where immunoreactivity was as intense as in the distal nerve segment. The identity of the ninjurin expressing cells as Schwann cells was confirmed by performing immunohistochemistry with antibodies to the Schwann cell marker S100 and demonstrating a similar pattern of staining (Data not shown). The ninjurin immunoreactivity was blocked by preincubation with the immunizing peptide, and the pattern of staining was consistent with the results of our in situ hybridization analysis.

In the central nervous system, cells with a morphology consistent with that of astrocytes were stained with the anti-ninjurin antibodies (Data not shown), but no neuronal staining was observed. To confirm the identity of these cells, simultaneous, dual label immunohistochemistry was performed using antibodies directed against glial fibrillary acidic protein (GFAP) and against ninjurin. In this analysis, ninjurin and GFAP immunoreactivity is present in the same cells, indicating that ninjurin is expressed predominantly by astrocytes.

In agreement with our RNA analysis, an immunohistochemical survey with anti-ninjurin antibodies confirmed that ninjurin is expressed in a wide variety of tissues in the adult rat, including the liver, kidney, thymus, uterus, adrenal gland, and dorsal root ganglia (Data not shown). In the dorsal root ganglia, ninjurin was not detected in neurons but was expressed in the satellite cells which ensheath the neuronal cell bodies. In the adrenal gland, ninjurin is expressed throughout the cortex and appears to be on the surface of the cortical cells. Ninjurin immunoreactivity was also observed on the surface of the hepatocytes of the liver. In the kidney, ninjurin was detected in the podocytes and/or mesangial cells of the glomerulus, but other renal cell types were negative. In the thymus, the thymocytes themselves were negative for ninjurin, but the thymic epithelial cells, which provide the proper microenvironment for lymphocyte maturation, stained intensely with the anti-ninjurin antibodies. Flat cells located on the surface of the thymic cortex and in the area adjacent to the blood vessels also expressed ninjurin. Staining for ninjurin was also observed in the uterus, where the ninjurin-positive cells were found in the myometrium. These cells were distinct from smooth muscle cells, and their distribution and morphology was consistent with fibroblasts of the associated connective tissues. Taken together, these results demonstrate that ninjurin immunoreactive cells are found in a wide variety of tissues.

Cell culture and transfection. Chinese hamster ovary (CHO) cells were cultured in F-12 medium supplemented with 10% fetal calf serum (FCS). T cell leukemia cells (Jurkat) were grown in RPMI1640 with 10% FCS. The expression vector pCMV-ninjurin was constructed by inserting the ninjurin cDNA into the plasmid pCMVneo (Brewer, C.B. (1994). Methods in Cell Biol. 43, 233–245). The pCMVneo or pCMV-ninjurin plasmids was transfected into CHO cells via calcium phosphate precipitation and into Jurkat cells via electroporation. Stable transfectants were selected by growth in medium containing G418 (400 $\mu$g/ml) and individual clones were isolated by limiting dilution. Primary cultures of sympathetic neurons from superior cervical ganglia (SCG) were prepared by dissecting tissue from E20–21 rat embryos as previously described (Martin et al., (1988) J. Cell. Biol. 106, 829–844). Primary cultures of neurons from dorsal root ganglia (DRG) were prepared from E17 rat embryos as previously described (Eichler et al., (1989) Brain Res 482, 340–346). Dissociated neurons were plated on confluent monolayers of either control CHO cells or CHO cell expressing ninjurin in 24-well plates. Cultures were grown in a medium which consists of 90% Eagles minimal essential medium (Gibco), 10% FCS, 20 $\mu$g/ml each of fluoro-deoxyuridine and uridine, and 50 ng/ml mouse NGF (gift from E. Johnson, Washington U.). Six hr after plating, the cells were fixed with 4% paraformaldehyde in PBS, and immunohistochemistry using anti-neurofilament H antibodies was performed. Following previously established criteria (Gennarini et al., (1991) Neuron 6, 595–606), approximately 50 neurites were chosen for measurement which each emerged from a single distinguishable cell body, were longer than the diameter of the neuronal cell body, and were identifiable over their entire length. The length of each neurite was measured after tracing them from the photomicrographs onto grided (2 mm) transparency film. Statistical analysis was performed using Sigma Plot (version 3.0).

Surface labeling of cells and immunoprecipitation of ninjurin. Cell surface proteins of the ninjurin transfected CHO cells were radioiodinated with $Na^{125}I$ (Amersham) using water-soluble Bolton-Hunter reagent (Pierce) as per manufacturer's instructions. Immunoprecipitation of ninjurin from these lysates was performed using anti-ninjurin antibodies as described previously (Fahrner et al., (1990) Mol. Cell. Biol. 10, 6454–6459). Immunoprecipitations were also performed using a monoclonal antibody directed against the cytoplasmic protein phospholipase C$\gamma$ I monoclonal antibody (Upstate Biotechnology, Inc.) as a control. $^{35}$S-labeled phospholipase C$\gamma$1 was immunoprecipitated from ninjurin transfected CHO cells grown in medium containing [$^{35}$S]methionine (120 mCi/ml final concentration, Amersham) for 16 hr.

The pattern of ninjurin immunoreactivity observed in the immunohistochemical analysis suggested that ninjurin was localized to the cell surface. This was most apparent in the adrenal gland and liver, where ninjurin immunoreactivity was clearly restricted to the adrenal cortical and hepatocyte cell surfaces, suggesting that ninjurin is either a membrane protein or possibly a secreted factor which adsorbs to the cell surface or extracellular matrix (data not shown). To further examine ninjurin localization, we attempted to immunoprecipitate it from cell lysate vs. medium conditioned by CHO cells expressing ninjurin. This experiment demonstrated that ninjurin was only present in the cell lysate (data not shown), suggesting that ninjurin is likely to be a membrane protein. To directly demonstrate that a portion of the ninjurin molecule is located outside of the cell, we labeled ninjurin expressing CHO cells with $^{125}$I using the Bolton-Hunter reagent under conditions which selectively label proteins on the cell surface (Thompson et al., (1987) Biochem. 26, 743–750). After labeling the cells, immunoprecipitations were performed with anti-ninjurin specific antibodies as well as with antibodies directed against the intracellular protein phospholipase C$\gamma$1, and the immunoprecipitated proteins were separated by gel electrophoresis and visualized by autoradiography (Data not shown). It is clear that the anti-ninjurin antibodies precipitated an intensely labeled 22 kD protein, whereas no signal was detected with the anti-phospholipase C$\gamma$1 antibody. Phospholipase C$\gamma$1 was effectively precipitated with this antibody using $^{35}$S-methionine-labeled cells (lane 5), indicating that are $^{125}$I labeling protocol did not label intracellular proteins. These results therefore strongly suggested that ninjurin is a plasma membrane protein, as predicted from sequence analysis.

Cell adhesion assays. The cell surface localization of ninjurin combined with its expression in glia after nerve injury and its expression in epithelial cells in a number of tissues suggested that it might be involved in cellular adhesion. Aggregation assays were performed using Jurkat cells (Shimizu et al., (1990) Nature 345, 250–253) stably transfected with pCMV-ninjurin or pCMVneo (nonrecombinant control). The cells were washed twice with RPMI1640 containing 5 mM Hepes buffer, suspended to a concentration of $2\times10^6$ cells/ml in RPMI1640 with 10% FCS, and 100 µl of the cell suspension were added to each well of a flat-bottomed 96-well microtiter plate. The formation of aggregates was examined after 1 hr using phase contrast microscopy. For demonstrating homophilic binding, aggregation experiments were performed using a mixture of ninjurin stable transfectants and non-transfected cells. The ninjurin positive cells were stained red with 1 mM CMTMR (5-(and-6)-(((4-chloromethyl)benzoyl)amino) tetramethylrhodamine) and control cells were stained green with 1 mM CMFTA (5-chloromethylfluoresceindiacetate) as described in the manufacturer's protocol (Molecular Probes). The cells were resuspended to $1\times10^6$ cells/ml, and 3 ml of the mixed cell suspension was allowed to form aggregates in 6-well culture plates. The composition of the aggregates was monitored by fluorescence microscopy.

Protein blot analysis was used to demonstrate that ninjurin is expressed in cells transfected with CMV-ninjurin, but is absent or present at very low levels in native Jurkat cells (data not shown). Incubation of ninjurin-expressing cells resulted in the formation of large aggregates that were readily demonstrable after 1 hr, whereas the control Jurkat cells formed only a few small aggregates (Data not shown). Aggregate formation depended on the presence of either Mg, Mn or Ca ions; no aggregates were detected when these assays were performed in the presence of 1 mM EDTA, suggesting that ninjurin mediated adhesion is dependent on divalent cations (data not shown).

For aggregation experiments using CHO cells, cells (ninjurin transfected and control) were harvested from confluent plates by treatment with trypsin, washed with F-12 medium, and resuspended at $1\times10^6$ cells/ml in F-12 with 10% FCS. Aggregation assays were performed on a rotary shaker at 80 rpm. Quantitation of aggregate formation was monitored at 15 min intervals by counting the number of particles using a hemocytometer (Takeichi, M. (1977). J. Cell. Biol. 75, 464–474). The extent of the aggregate formation is inversely proportional to the number of particles, and was determined by calculating an index $N_1/N_0$, where $N_1$ and $N_0$ were the total particle numbers at incubation times t and 0, respectively (Takeichi, 1977). All of the aggregation experiments were performed at 37° C.

A decrease in the number of particles with time was observed with the transfected cells, indicating the formation of larger aggregates with ninjurin-expressing cells (data not shown) (Takeichi, 1977). These results provide further support that ninjurin is involved in cellular adhesion as its effects are observed in multiple cell types.

To determine whether the adhesion mediated by ninjurin could occur via a homophilic mechanism, aggregation experiments on mixtures of transfected and non-transfected Jurkat cells that were differentially stained with fluorescent dyes were performed. Equal amounts of ninjurin-positive cells (colored red) and control cells (colored green) were mixed together and the resulting aggregates were examined by fluorescence microscopy. The aggregates consisted predominantly of red, ninjurin-positive cells, with some non-transfected cells adhering to the surface (Data not shown). None of the aggregates were composed primarily of non-transfected cells, nor wer aggregates with a mosaic pattern of the two cell types observed.

The demonstration that ninjurin can mediate adhesion via homophilic binding, encouraged us to investigate its expression on neurons, as it may play an important role in nerve regeneration. We therefore examined cultures of sympathetic neurons dissected from the superior cervical ganglia (SCG) of E21 rat pups. After culturing the neurons for 5 days in NGF and the anti-mitotic bromodexoyuridine (to remove non-neuronal cells), immunohistochemical analysis was performed using either anti-ninjurin or anti-neurofilament H antibodies (Data not shown). The pattern of staining for these two molecules is very similar, with intense immunoreactivity present in the cell bodies and extending out into the axonal projections. The co-localization of ninjurin with neurofilament H, along with the detection of ninjurin immunoreactivity in the neuronal projections, indicates that ninjurin is present in locations where ninjurin homophilic binding could occur between Schwann cells and neurons.

Ninjurin is expressed by DRG neurons after injury and is transported to the site of injury. To promote nerve regeneration via homophilic binding, ninjurin should be expressed by neurons as well as Schwann cells after nerve injury. To examine this possibility, ninjurin expression was examined in the dorsal root ganglion (DRG) after sciatic nerve transection.

Immunohistochemistry with anti-ninjurin antibodies revealed that ninjurin was detectable 1 day after nerve transection in the DRG neuronal cell bodies (Data not shown). Ninjurin expression was not detected in DRG neurons from the contralateral uninjured side, suggesting that neuronal synthesis of ninjurin is induced by axotomy. We next tested whether ninjurin was anterogradely transported down the axon. For this purpose, the sciatic nerve was ligated and 5 to 8 mm distal to the ligation site the nerve was transected. As a control, sciatic nerves were ligated but no axotomy was performed. After 1 day, the nerves were harvested and ninjurin was detected using immunohistochemistry. Ninjurin staining was intense proximal to the ligation site in the nerve that had been transected (Data not shown), suggesting that ninjurin had been transported down the axon. In contrast, only a minor amount of ninjurin staining was observed around the ligation site in the non-transected nerve, presumably representing a local response to the ligation itself. Taken together, these results indicate that ninjurin is upregulated in neurons after nerve injury and is subsequently anterogradely transported to the site of injury, where ninjurin is also expressed by Schwann cells.

Ninjurin promotes neurite outgrowth from DRG neurons cultured in vitro.

To test directly whether ninjurin can promote neurite outgrowth, we examined DRG neuron/CHO cell co-cultures as previously used to analyze promotion of neurite outgrowth by neuronal F3 glycoprotein (Gennarini et al., 1991) and NCAM (Doherty et al., (1989) J. Cell Biol. 109, 789–798). DRGs from E17 rat embryos were dissected, dissociated and plated at low density onto confluent monolayers of either CHO cells expressing ninjurin or control CHO cells. Six hr after plating, the cells were fixed and stained with antibodies to neurofilament H to visualize the neurites. Representative photomicrographs of these cultures demonstrate an increase in neurite outgrowth from neurons cultured on CHO cells expressing ninjurin (Data not shown). To quantitate this effect, approximately 50 neurons were randomly selected from each growth condition, and the length of the longest neurite per neuron, which did not have contacts with nearby neurons, was measured. Neurons grown for 6 hr on CHO cells expressing ninjurin had neurites with an average length of $569\pm134$ µm, whereas neurites from neurons grown on control CHO cells were $297\pm104$ µm in length. These results indicate that ninjurin promotes an increase in the extent of neurite outgrowth.

Example 2

Characterization of the binding domain of ninjurin

To directly investigate whether the N-terminal extracellular hydrophilic region is responsible for the observed homophilic adhesion, partially overlapping synthetic peptides whose sequences collectively encompass the entire predicted ninjurin extracellular domain were tested for their ability to inhibit the ninjurin- mediated adhesion. Aggregation assays with the ninjurin-expressing Jurkat cell transfectants were performed, and the degree of aggregation was examined after 60 minutes by measuring the number of cells incorporated in aggregates. Peptide 2 inhibited aggregation at a concentration of 0.1 mg/ml, and aggregation was completely abolished at concentrations above 1 mg/ml. In constrast, peptides 1 and 4 had no effect on aggregation at either of these concentrations. These results indicate that the ninjurin amino terminus is indeed located extracellularly, and that residues 16 to 45 (sequence which corresponds to peptide 2) contains a domain that is critical for binding.

To further delimit the site of interaction, an additional 4 peptides (peptides 5 through 8) were tested for their ability to inhibit ninjurin-mediated aggregation (Data not shown). A peptide corresponding to ninjurin residues 26 to 37 showed inhibitory activity comparable to peptides 2 or 3. Inhibition of aggregation was observed at concentrations higher than 0.4 mg/ml and was completely abolished at concentrations above 2 mg/ml. To identify the amino acids most critical for ninjurin-mediated adhesion, peptides (9–15) stretching from residue 26 to 37, each containing single amino acid mutations, were tested in the aggregation assay. The ability of each of these peptides to inhibit ninjurin-mediated adhesion in a dose-dependent manner was examined. The seven residues between prolines 27 and 35 (P27 and P35) were most important. Mutation of the Arg or Trp residues resulted in dramatic decreases in the ability to inhibit aggregation, implying that these 4 residues play an important role in ninjurin-ninjurin molecular contact. Mutations made to the non-charged residues including Gly-30, Leu-31 and Asn-33 did not alter the ability to inhibit aggregation, indicating that these residues are not critical to the interaction. Curiously, one of the mutations (Asn-33 to Leu33) resulted in a peptide with greater inhibitory activity than wild type, suggesting that it interacts with ninjurin very strongly.

The ninjurin adhesion motif contains a tryptophan and a cluster of arginine residues. None of the previously reported homophilic adhesion molecules contains this peptide motif, or a combination of tryptophan and arginines as functionally relevant residues. The peptide inhibition experiments showed that the replacement of tryptophan by alanine dramatically decreased the peptide's inhibitory effect, suggesting that this tryptophan residue plays a major role in ninjurin-ninjurin interactions. This tryptophan residue may be directly involved in the physical interaction between ninjurin molecules, or, perhaps, it is necessary for the overall structure of the domain. Replacement of the arginines showed significant but less dramatic effects on ninjurin adhesion. Although these arginines appear to be essential, direct interactions between these positively charged residues on opposing molecules seems unlikely. Perhaps these residues contribute to ninjurin adhesion indirectly by neutralizing negatively charged regions elsewhere within the molecule. Interestingly, even though ninjurin binding is dependent on divalent cations, the ninjurin adhesion motif does not contain acidic residues commonly associated with cation binding motifs. Overall ninjurin contains 13 Glu and Asp residues, with 6 of these located within the amino terminal 23 residues. Perhaps this acidic region is related to ninjurin's cation dependence and thus plays a role in the formation of the functional ninjurin adhesion domain.

The demonstration that the inhibitory peptide we identified via cell aggregation assays was able to reverse the ninjurin-stimulated neurite outgrowth from neurons indicates that the biological function of ninjurin is related to its adhesive properties. In addition, the basal adhesion observed for wild type Jurkat cells was abolished in the presence of peptides containing ninjurin's adhesion motif (data not shown). This suggests that other molecule(s) expressed by Jurkat cells possibly share the ninjurin adhesion motif. If other molecules with the ninjurin-like adhesion motif exist, then the possibility that ninjurin may participate in heterophilic interactions as well homophilic interactions must be considered. This would greatly extend the number of interactions, and potentially the number of functions, in which ninjurin is involved.

Our expression analysis revealed that ninjurin is present in a wide variety of tissues (e.g. thymus, kidney, liver, adrenal gland) in addition to the nervous system and is predominantly expressed in epithelial cells, suggesting ninjurin is important in the development and/or function of a number of tissues. For instance, its presence in the thymus may indicate a role in thymocyte development, as adhesion molecules on thymic epithelial cells are thought to be important in this process (Patel et al., (1993) Immunol 5, 283–292). The isolation of ninjurin and its identification as a new adhesion protein that is expressed in a number of tissues during embryogenesis as well as adulthood suggest that it may play an important role in the proper development and function of a variety of tissues, in addition to its role in nerve regeneration.

Ninjurin mutants fail to support aggregation. Aggregation inhibition experiments using synthetic peptides revealed that residues 26 to 37 (the ninjurin adhesion motif) are responsible for ninjurin-mediated homophilic cellular adhesion. However, these current results do not distinguish whether homophilic interactions result from (1) a direct interaction between this motif on two ninjurin molecules or (2) an interaction with this motif and another region on the second ninjurin molecule. To investigate these possibilities, Jurkat cell lines expressing ninjurin molecules containing a double mutation (Arg28 to Asn and Asn29 to Ala) in the ninjurin adhesion motif was generated. Protein blot and immunohistochemical analyses of these cell lines confirmed that the expression levels for wild type and mutant ninjurin molecules were comparable, and that the ninjurin mutants were expressed on the cell surface (Data not shown). Assays with these ninjurin transfected cell lines revealed that Jurkat cells stably expressing either of the ninjurin mutants showed no increase in aggregation over native Jurkat cells (Data not shown). These results demonstrate that the motif identified using peptides and aggregation inhibition is clearly necessary for ninjurin-mediated adhesion. To determine whether the mutant molecules could interact with wild type ninjurin, we performed aggregation assays on mixtures of cells expressing either wild type or mutant ninjurin molecules. When equal amounts of the two types of cells were mixed together, the aggregates contained predominantly wild type ninjurin-expressing cells (Data not shown). A mosaic pattern, containing equivalent amounts of the two types of cells, was not observed. Taken together, these results indicate that interactions between the ninjurin adhesion motif (residues 26 to 37) on both ninjurin molecules are responsible for the homophilic adhesion mediated by ninjurin.

Ninjurin-stimulated neurite outgrowth is mediated through the adhesion motif. To determine whether the ninjurin promotion of neurite extension from primary DRG neurons occurs via ninjurin's adhesive properties, the peptides were tested for the ability to inhibit neurite outgrowth. DRG neurons from E17 rat embryos were dissociated and seeded onto confluent monolayers of CHO cells, either native or expressing ninjurin. The neuronal cultures were treated with peptides (0.5 mg/ml) corresponding to either the native or mutant sequences of the ninjurin adhesion motif, and neurite extension was monitored. As expected, neurites from neurons grown on CHO cells expressing ninjurin showed increased neurite outgrowth compared to those grown on native CHO cells. However, the neurite outgrowth promoting effect of ninjurin was inhibited when neurons were treated with the peptide of native sequence, whereas the peptide containing a mutation in this sequence (PPRWGLRNRPIN) (SEQ ID NO: 21) had no significant inhibitory effect on neurite extension by DRG neurons. These results indicate that the adhesion motif is required for ninjurin-stimulated neurite outgrowth, suggesting that the adhesive properties of ninjurin play an important functional role in this process.

Example 3

Cloning of human ninjurin proteins

Rat ninjurin nucleic acid sequence was used to search for homologous sequence in the EST database by basic local alignment search tool (BLAST: Altschul, S. F., et al. J. Mol. Biol. 215:403–410, 1990). Human EST clones yd37d12 (T84142, T89382) and yu87c07(H91351, H91056), yf8b06 (R06312, R06257), yd98c05 (T89765, T89491) were obtained. The nucleotide sequences of the entire clones were determined. All nucleotide sequencing was performed using fluorescent dye terminator technology per manufacturer's instructions on an Applied Biosystems automated sequencer model#373 (Applied Biosytstems, Foster City, Calif.). Plasmid DNA for sequencing was prepared by using Wizard Miniprep kit (Promega Corp., Madison, Wis.) according to the manufacturer's instructions. To obtain 5' end of each of the clones, oligonucleotide primers corresponding to the reverse complementary sequence of the human EST clones (yd37d12, and yu87c07) were used for the rapid amplification of the cDNA ends (RACE) technique (Frohman, M.A. Methods in Enzymology 218:340–356, 1993) using the Human Brain (for ninjurin1-variant, ninjurin2) and Human Adrenal (for ninjurn1) Marathon RACE kit (CLONTECH, Palo Alto, Calif.) per manufacturer's instructions with minor modifications. Briefly, using nested reverse primers for ninjurinl (#40365: 5'-AGGGCAGGCAGCATCCAGGGTCCT (SEQ ID NO: 28), and #40373: 5'-TGTCCGGGTTGTTAAGG-TCGTACTT) (SEQ ID NO: 29) and ninjurin2(#30741: 5'-GAAGACCAAGATGGTGGCTGCGTTG (SEQ ID NO: 30) and #10348:5'-TTCAGGTTCAGCCGTGCAAT-GACCA) (SEQ ID NO: 31 ) in combination with the primers to the adaptor at cDNA ends (AP1, AP2; provided in the kit), the 5' end of the ninjurin 1 and ninjurin 2 were amplified by two successive PCR reactions using the following parameters. For ninjurin1: using human adrenal cDNA as a template, 1st reaction: #40365 and AP1, 94C. for 2 min, 68 C. for 30 sec and 68C. 2 min, followed by decreasing anealing temperature by 0.5 C. per each cycle for 16 cycles, then 94 C. 2 min, 60 C. 30 sec, and 68 C. for 2 min for 20 cycles. 2nd reaction: #40373 and AP2, 94 C. for 2 min, 68 C. for 2 min 30 sec for 25 cycles. For ninjurin 2, human brain cDNA was used as a template with 1st reaction:#30741 and AP1, 94 C. for 30 sec, 68 C. for 30 sec, and 68 C. for 2 min, followed by decreasing anealing temperature by 0.5 C. per each cycle for 19 cycles, then 94 C. 2 min, 58 C. 30 sec and 68 C. for 2 min for 20 cycles. 2nd reaction: #10348 and AP2: 94 C. for 30 sec, 72 C. for 2 min for 5 cycles, 94 C. for 30 sec, 70 C. for 2 min for 5 cycles, and 94 C. for 30 sec, 68 C. for 2 min for 25 cycles.) The RACE-PCR products after secondary PCR were cloned into pBluescript KS+ and sequenced. The resulting sequence of ninjurin 2 was different from the sequence of the clone yu87c07 at its 5' end, and the RACE-PCR product was termed ninjurin2 and the clone yu87c07 was termed variant 2 of ninjurin 2. The nucleotide sequence of the clone yd98c05 was identical to the sequence of ninjurin1 only in its 3' end region, and termed as ninjurin1-variant. The nucleotide sequence of the clone yf08b06 was identical to the sequence of ninjurin 2 only in its 3' end region, and termed as ninjurin2-variant 1. Nested reverse primers specific to the ninjurin 1-variant (#30749: 5'-TCAGTCGCATTTAGGATGAGTTTTG (SEQ ID NO: 32), and #10391: 5'-GGATGAGTTTTGTCGCCCA-GAGAA) (SEQ ID NO: 33) were synthesized and used for RACE-PCR to amplify 5' end of the ninjurinl-variant cDNA (1st PCR: #30749 and AP1, 94 C. for 30 sec, 68 C. for 30 sec, and 68 C. for 2 min, followed by decreasing anealing temperature by 0.5 C. per each cycle for 19 cycles, then 94 C. 2 min, 58 C. 30 sec and 68 C. for 2 min for 20 cycles, 2nd PCR: #10391 and AP2, 94 C. for 30 sec, 72 C. for 2 min for 5 cycles, 94 C. for 30 sec, 70 C. for 2 min for 5 cycles, and 94 C. for 30 sec, 68 C. for 2 min for 25 cycles). The RACE-PCR product after secondary PCR was cloned into pBluescript KS+ and sequenced.

We claim:

1. A recombinant nucleic acid comprising a nucleic acid molecule encoding a ninjurin protein having at least 70% homology to a sequence selected from the group consisting of the sequence of FIG. 1B (SEQ ID NO: 4), FIG. 2B (SEQ ID NO: 6), and FIG. 3B (SEQ ID NO: 8).

2. A recombinant nucleic acid according to claim 1 wherein said ninjurin protein is ninjurin 1.

3. A recombinant nucleic acid according to claim 1 wherein said ninjurin protein is ninjurin 2.

4. A recombinant nucleic acid according to claim 1 wherein said ninjurin protein is a human ninjurin protein.

5. A recombinant nucleic acid according to claim 1 wherein said ninjurin protein has at least 85% homology to a sequence selected from the group consisting of the sequence of FIG. 1B (SEQ ID NO: 4), FIG. 2B (SEQ ID NO: 6), and FIG. 3B (SEQ ID NO: 8).

6. A recombinant nucleic acid according to claim 1 wherein said ninjurin protein has at least 90% homology to a sequence selected from the group consisting of the sequence of FIG. 1B (SEQ ID NO: 4), FIG. 2B (SEQ ID NO: 6), and FIG. 3B (SEQ ID NO: 8).

7. A recombinant nucleic acid according to claim 1 wherein said ninjurin protein has at least 95% homology to a sequence selected from the group consisting of the sequence of FIG. 1B (SEQ ID NO: 4), FIG. 2B (SEQ ID NO: 6), and FIG. 3B (SEQ ID NO: 8).

8. A host cell comprising the nucleic acid of claim 1.

9. A recombinant nucleic acid encoding the amino acid sequence depicted in FIG. 1B (SEQ ID NO: 4).

10. A recombinant nucleic acid encoding the amino acid sequence depicted in FIG. 2B (SEQ ID NO: 6).

11. A recombinant nucleic acid encoding the amino acid sequence depicted in FIG. 3B (SEQ ID NO: 8).

12. A recombinant nucleic acid comprising the nucleic acid depicted in FIG. 1A (SEQ ID NO: 3).

13. A recombinant nucleic acid comprising the nucleic acid depicted in FIG. 2A (SEQ ID NO: 5).

14. A recombinant nucleic acid comprising the nucleic acid depicted in FIG. 3A (SEQ ID NO: 7).

15. A recombinant nucleic acid comprising the nucleic acid depicted in FIG. 4 (SEQ ID NO: 9).

16. A recombinant nucleic acid comprising the nucleic acid depicted in FIG. 4 (SEQ ID NO: 10).

17. A recombinant nucleic acid comprising the nucleic acid depicted in FIG. 6 (SEQ ID NO: 11).

* * * * *